US007432425B2

(12) United States Patent
Dixon et al.

(10) Patent No.: US 7,432,425 B2
(45) Date of Patent: Oct. 7, 2008

(54) ISOFLAVONOID METHYLATION ENZYME

(75) Inventors: Richard A. Dixon, Ardmore, OK (US);
Xian Z. He, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 348 days.

(21) Appl. No.: 11/071,964

(22) Filed: Mar. 4, 2005

(65) Prior Publication Data
US 2005/0150010 A1 Jul. 7, 2005

Related U.S. Application Data

(62) Division of application No. 09/926,571, filed as application No. PCT/US00/13389 on May 15, 2000, now Pat. No. 6,878,859.

(60) Provisional application No. 60/135,026, filed on May 20, 1999.

(51) Int. Cl.
*C12N 15/29* (2006.01)
*C12N 15/52* (2006.01)
*C12N 15/82* (2006.01)
*A01H 5/00* (2006.01)

(52) U.S. Cl. .................. 800/313; 800/298; 800/312; 435/419

(58) Field of Classification Search .................. 800/278, 800/279, 298; 536/23.1, 23.2, 23.6
See application file for complete search history.

(56) References Cited

U.S. PATENT DOCUMENTS 4,704,400 A 11/1987 Miller et al. ................ 514/454

FOREIGN PATENT DOCUMENTS

WO WO 93/23069 11/1993
WO WO 00/37656 6/2000

OTHER PUBLICATIONS

He X. and Dixon R., The Plant Cell, Sep. 2000; vol. 12 pp. 1689-1702.*
Zubieta C. et al. Nature Structural Biology, 2001, vol. 8, No. 3; pp. 271-279.*
Edwards and Dixon, "Isoflavone O-methyltransferase activities in elicitor-treated cell suspension cultures of *Medicago sativa*," *Phytochemistry*, 30:2597-2606, 1991.
Khouri et al., "Partial purification, characterization, and kinetic analysis of isoflavone 5-O-methyltransferases from yellow lupin roots," *Arch. Biochem. Biophys*, 262:592-598, 1988.
Wengenmayer, et al., "Purification and properties of a S-adenosylmethionine: isoflavone 4'-O-methyltransferase from cell suspension cultures of *Cicer arietinum* L," *Eur. J. Biochem.*, 50:135-143, 1974.
Adlercreutz, et al., "Urinary excretion of ligans and isoflavonoid phytoestrogens in Japanese men and women consuming a traditional Japanese diet," *Am J Clin Nutr* 54: 1093-1100, 1991.

Adlercreutz and Mazur. "Phyto-estrogens and western diseases," *Ann Mes* 29: 95-120, 1997.
An, "Development of plant promoter expression vectors and their use for analysis differential activity of nopaline synthase promoter is transformed tobacco cells," *Plant Physiol* 81: 86-91, 1986.
Angell and Baulcombe, "Consistent gene silencing in transgenic plants expressing a replicating potato virus X RNA," *EMBO J* 16: 3675-3684, 1997.
Barnes et al., "Soybeans inhibit mammary tumors in models of breast cancer." In M.W. Puriza, eds, *Mutagenes and Carcinogens in the Diet*, Wiley-Liss, Inc, New York, pp. 239-253, 1990.
Batard et al., "Molecular cloning and functional expression in yeast of CYP76B1, a xenobiotic-inducible 7-ethoxycoumarin O-deethylase from *Helianthus tuberosus,*" *Plant J*, 14: 111-120, 1998.
Bhattacharyya. and Ward, "Biosynthesis and metabolism of glyceollin I in soybean hypocotyls following wounding or inoculation with *Phytophthora megasperma* f. sp. *Glycinea,*" *Physiol Mol Plant Pathol* 31:387-405, 1987.
Bourque, "Antisense strategies for genetic manipulations in plants," *Plant Sci* 105: 125-149, 1995.
Broun et al., "Catalytic plasticity of fatty acid modification enzymes underlying chemical diversity of plant lipids," *Science*, 282:1315-1317, 1998.
Bugos et al., "cDNA cloning, sequence analysis and seasonal expression of lignin-bispecific caffeic acid/5-hydroxyferulic acid O-methyltransferase of aspen," *Plant Mol Biol*, 17: 1203-1215, 1991.
Dalkin et al., "Stress responses in alfalfa (*Medicago sativa* L.) I. Elicitor-induction of phenylpropanoid biosynthesis and hydrolytic enzymes in cell suspension cultures," *Plant Physiol*, 92: 440-446, 1990.
Dewick and Martin, "Biosynthesis of pterocarpan, isoflavan and coumestan metabolites of *Medicago sativa* : chalcone, isoflavone and isoflavanone precursors," *Phytochemistry* 18: 597-602, 1979.
Dewick and Martin, "Biosynthesis of pterocarpan and isoflavan phytoalexins in *Medicago sativa*: the biochemical interconversion of pterocarpans and 2'-hydroxyisoflavans," *Phytochemistry*, 18: 591-596, 1979.
Dixon et al., "Prospects for the metabolic engineering of bioactive flavonoids and related phenylpropanoid compounds," *Adv Exp Med and Biolog*, 439:55-66, 1998.
Dixon et al., "Molecular controls for isoflavonoid biosynthesis in relation to plant and human health," *Recent Advances in Phytochemistry*, 33: 133-160, 1999.
Dixon, "Isoflavonoids: biochemistry, molecular biology and biological functions." In U. Sankawa, eds, *Comprehensive Natural Products Chemistry*, Elsevier, pp. 773-823, 1999.

(Continued)

*Primary Examiner*—Russell Kallis
(74) *Attorney, Agent, or Firm*—Sonnenschein Nath & Rosenthal LLP

(57) ABSTRACT

Methods of genetically manipulating biology active 4'-O-methylated isoflavonoids have been found based upon the regiospecifity of isoflavone 7-OMT in vivo. Upon transformation and expression of an isoflavonoid O-methyltransferase gene, up-regulation of IOMT in the transgenic plants can be used to increase the accumulation of 4'-O-methylated isoflavonoid phytolalexins, providing for increased disease resistance to the plant. Similar methods can be used to increase accumulation of 4'-O-methylated isoflavonoid nutraceuticals in plants. For down-regulation of IOMT in plants that naturally make 4'O-isoflavonoid phytoalexins and 4'-O-methylated isoflavonoid nutraceuticals, IOMT gene sequences can be transformed in the antisense orientation.

10 Claims, 11 Drawing Sheets

OTHER PUBLICATIONS

Dixon and Paiva, "Stress-induced phenylpropanoid metabolism," *Plant Cell*, 7: 1085-1097, 1995.

Dixonand Harrison, "Activation, structure and organization of genes involved in microbial defense in plants," *Adv Genet*, 28: 165-234, 1990.

Edwards et al., "A simple and rapid method for the preparation of plant genomic DNA for PCR analysis," *Nucleic Acids Res*, 19: 1349, 1991.

Frick and Kutchan. "Molecular cloning and functional expression of O-methyltransferases common to isoquinoline alkaloid and phenylpropanoid biosynthesis," *Plant J*, 17: 329-339, 1999.

Gauthier et al., "cDNA cloning and characterization of a 3'/5'-O-methyltransferase for partially methylated flavonols from *Chrysosplenium americanum*," *Plant Mol Biol*, 32: 1163-1169, 1996.

Gauthier et al., "Characterization of two cDNA clones which encode O-methyltransferases for the methylation of both flavonoid and phenylpropanoid compounds," *Arch Biochem Biophys*, 351: 243-249, 1998.

Hadwiger and Webster., "Phytoalexin production in five cultivars of pea differentially resistance to three races of *Pseudomonas syringae* pv. Pisi," *Phytopathology*, 74: 1312-1314, 1984.

Hakamatsuka et al., "P-450-dependent oxidative rearrangement in isoflavone biosynthesis: reconstitution of P-450 and NADPH:P450 reductase", *Tetrahedron*, 47: 5969-5978, 1991.

Hakamatsuka et al., "Purification of 2-hydroxyisflavanone dehydratase from the cell cultures of *Pueraria lobata*," *Phytochemistry*, 49: 497-505, 1998.

He et al., "Stress responses in alfalfa (*Medicago sativa* L.) XXII. cDNA cloning and characterization of an elicitor-inducible isoflavone 7-O-methyltransferase," *Plant Mol Biol*, 36: 43-54, 1998.

He and Dixon, GenBank accession No. AF023481 see also *Plant Physiology* vol. 115, p. 1289, 1997.

He and Dixion, "Affinity chromatography, substrate/product specificity and amino acid sequence analysis of an isoflavone O-methyltransferase from alfalfa (*Medicago sativa* L.)," *Arch Biochem Biophys*, 336: 121-129, 1996.

Higgins, "Role of the phytoalexin medicarpin in three leaf spot diseases of alfalfa," *Physiol Plant Pathol*, 2:289-300, 1972.

Horsch et al., "A simple and general method for transferring genes into plants," *Science*, 227: 1229-1231, 1985.

Ibrahim et al., "Enzymology and compartmentation of polymethylated flavonol glucosides in *Chrysasplenium americanum*," *Phytochemistry*, 26: 1237-1245, 1987.

Ibrahim et al., "Plant O-methyltransferases: molecular analysis, common signature and classification," Plant Mol Biol 36: 1-10, 1998.

Ingham et al., "Fungitoxic isoflavones from *Lupinus albus* and other *Lupinus* species," *Zeitschrift fur Naturforschung*, C38: 194-200, 1983.

Joshi and Chiang, "Conserved sequence motifs in plant S-adenosyl-L-methionine-dependent methyltransferases," *Plant Mol. Biol*, 37: 663-674, 1998.

Jung et al., "Identification and expression of isoflavone synthase: the key enzyme for biosynthesis of isoflavones in legunmes," *Nature Biotechnology*, 18:208-212, 2000.

Kessmann et al., "Stress responses in alfalfa (*Medicago sativa* L.) III. Induction of medicarpin and cytochrome P450 enzyme activities in elicitor-treated cell suspension cultures and protoplasts," *Plant Cell Rep*, 9: 38-41, 1990.

Kistler and VanEtten, "Regulation of pisatin demethylation in *Nectria haematococca* and its influence on pisatin tolerance and virulence," *J Gen Micro*, 130: 2605-2613, 1984.

Klein et al., "Stable genetic transformation of intact *Nicotiana* cells by the particle bombardment process," *Proc Natl Acad Sci USA*, 85: 8502-8505, 1998.

Kochs and Grisebach, "Enzymatic synthesis of isoflavones," *Eur J Biochem*, 155: 311-318, 1986.

Lamb et al., "Emerging strategies for enhancing crop resistance to microbial pathogens," *Bio/technology*, 10: 1436-1445, 1992.

Lee et al., "Dietary effects on breast-cancer risk in Singapore," *Lancet*, 337: 1197-1200, 1991.

Li et al., "5-Hydroxyconiferyl aldehyde modulates enzymatic methylation for syringyl monolignol formation, a new view of monolignol biosynthesis in angiosperms," *J Biol Chem*, 275: 6537-6545, 2000.

Long et al., "Further studies on the relationship between glycollin accumulation and the resistance of soybean leaves to *Pseudomonas syringae* pv. *Glycinea*," *Phytopathology*, 75: 235-239, 1985.

Matzke and Matzke,. "How and why do plants inactivate homologous (trans)genes?" *Plant Physiol*, 107: 679-685, 1995.

Moesta and Grisebach,, "L-2-Aminooxy-3-phenylpropionic acid inhibits phytoalexin accumulation in soybean with concomitant loss of resistance against *Phytophthora megasperma* f. sp. *Glycinea*," *Physiol Plant Pathol*, 21: 65-70, 1982.

Murashige and Skoog, "A revised media for rapid growth and bioassay with tobacco tissue culture," *Physiol Plant*, 15:473-497, 1962.

Paiva et al., "Regulation of isoflavonoid metabolism in alfalfa," *Plant Cell, Tissue and Organ* Cult, 38: 213-220, 1994.

Rahe, "Occurrence and levels of the phytoalex in phasecollin in relation to delimination at sites of infection of *Phaseolus vulgaris* by *Colletotrichum lindemuthianum*," *Can J Botany*, 51: 2423-2430, 1973.

Restrepo et al., "Nuclear transport of plant polyviral proteins," *Plant Cell*, 2: 987-998, 1990.

Sambrook et al. *Molecular Cloning A Laboratory Manual* (2nd Ed), Cold Spring Harbor Laboratory Press, New York: pp. 1.53-1.110, 1989.

Shorrosh et al., "Molecular cloning, characterization and elicitation of acetyl-CoA carboxylase in alfalfa," *Proc Natl Acad Sci USA*, 91:4323-4327, 1994.

Shutt, "The effects of plant oestrogens on animal reproduction," *Endeavour*, 75: 110-113, 1976.

Steele et al., "Molecular characterization of the enzyme catalyzing the aryl migration reaction of isoflavonoid biosynthesis in soybean," *Arch Biochem Biophys*, 367: 146-150, 1999.

Summer et al., "High-performance liquid chromatography/continuous-flow liquid secondary ion mass spectrometry of flavonoid glucosides in leguminous plant extracts," *J. Mass Spectrom*, 31:472-485, 1996.

Thomas et al., "Selection of interspecific somatic hybrids of *Medicago* by using Agrobacterium—transformed tissue," *Plant Sci*, 69: 189-198, 1990.

VanEtten et al., "Two classes of plant antibiotics: phytoalexins versus phytoanticipins," *The Plant Cell*, 6:1191-1192, 1994.

Wong, and Francis, "Flavonoids in genotypes of *Trifolium subterraneum*-II. Mutants of the Geraldton variety," *Phytochemistry*, 7: 2131-2137, 1968.

Yanagihara et al., "Antiproliferative effects of isoflavones on human cancer cell lines established from the gastrointestinal tract," *Cancer Res*, 53: 5815-5821, 1993.

Zhou-Jin Rong et al., "Inhibition of murine bladder tumorigenesis by soy isoflavones via alterations in the cell cycle, apoptosis, and angiogenesis," *Cancer Res*, 58: 5231-523, 1998.

Deavours et al., "Functional analysis of members of the isoflavone and isoflavonone O-methyltransferase enzyme families from the model legume *Medicago truncatla*," *Plant Mol. Biol.*, 62:715-733, 2006.

Liu et al., "Elicitor-induced association of isofavone O-methyltransferase with endomembranes prevents the formation and 7-O-methylation of daidzein during isofavonoid phytoalexin biosynthesis," *The Plant Cell*, 13:2643-2658, 2001.

Tasdemir et al., "Antitrypansosomal and antileishmanial activities of flavonoids and their analogues: in vitro, in vivo, structure-activity relationship, and quantitative structure-activity relationship studies," *Antimocrobial Agents and Chemotherapy*, 4:1352-1364, 2006.

* cited by examiner

```
ccaaattcca tttgaaaaaa aaaaatggct tcatcaatta atggccgaaa accaagtgaa  60
attttcaaag cacaagcttt attatacaaa catatatatg ccttcataga ttccatgtct 120
cttaaatggg ctgttgaaat gaacatacca aacataatcc aaaaccatgg caaaccaatt 180
tctctttcaa acttagtttc aattcttcaa gttccatcgt cgaaaatagg taacgtgcgg 240
cgtctcatgc gttacctcgc gcacaacgga ttcttcgaga taattacaaa agaagaagag 300
tcttatgctc tcactgttgc ttcagagctt cttgttagag gcagtgatct ttgtttagca 360
ccaatggttg agtgtgttct tgatccaact ctttcgggtt cgtatcatga gctgaagaaa 420
tggatttatg aggaagatct tacactcttt ggtgttactt taggatctgg ttttgggat 480
tttcttgata aaaatcctga atataatacc tcatttaatg atgcaatggc tagtgattct 540
aaattgataa acttggcatt gagagattgt gattttgtgt tgatggatt ggaatcaatt 600
gtggatgttg gtggtggaac tggaacaact gctaagatta tttgtgagac ttttcctaag 660
ttgaaatgta ttgtgtttga taggccacaa gttgtagaga acttatctgg aagcaataat 720
ttgacttatg ttggtgggga catgttcaca tctattccta atgctgatgc agttttgctt 780
aagtatattc tacataattg gactgataag gattgcctaa ggatactgaa gaaatgtaaa 840
gaagctgtta caaatgatgg gaaaagagga aaagtgacta ttatagacat ggtgatagat 900
aaaaaaaaag atgagaatca agttactcaa attaagctcc ttatggatgt aaacatggct 960
tgtctaaatg gaaaagagag aaatgaggaa gaatggaaga aactcttcat agaagctggt 1020
ttccaacact ataagatatc tcctttgact ggatttttgt ctcttattga gatctatcca 1080
taaacacttt tgctttgatc attcatccat tctattgttt catgttataa accaatcttg 1140
ttctctatta tgatatctca cttgtaatat gcatttgttg gtaacaaata atagaatttg 1200
catacatgta tgatttttaa aaaaaaaaa a                                 1231
```

Fig. 2

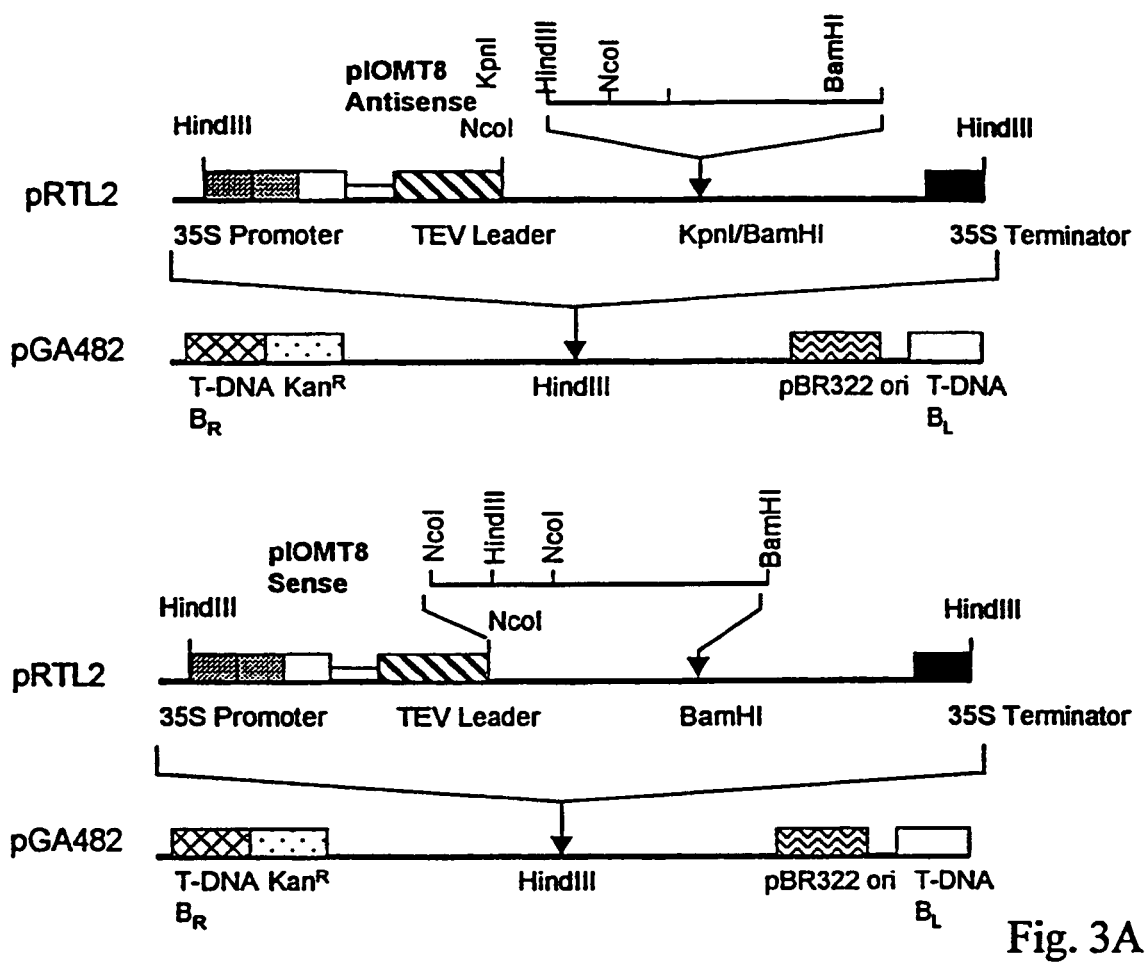
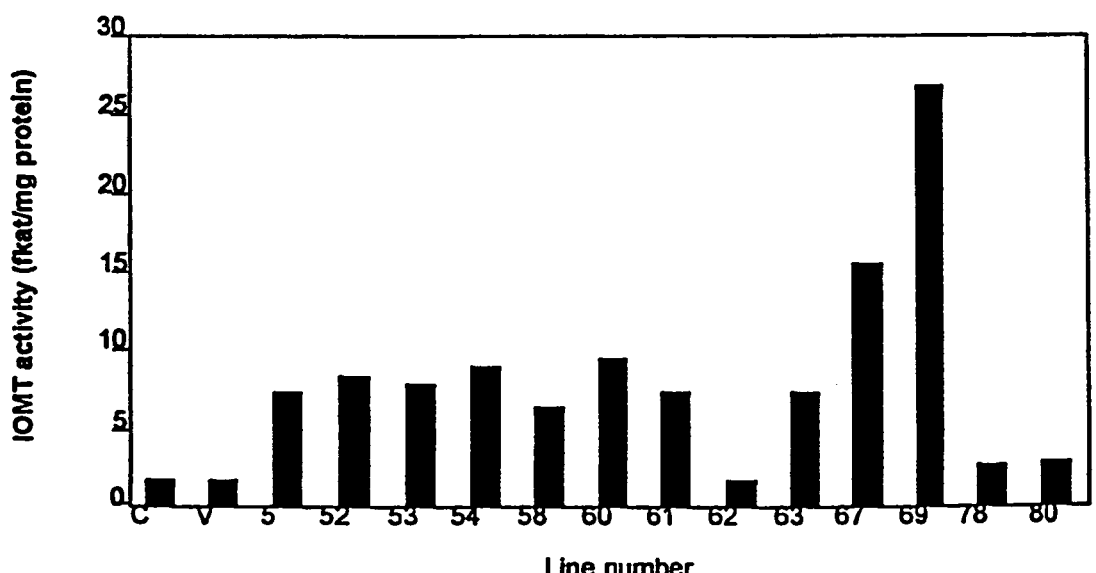
Fig. 3A
Fig. 3B

SEQUENCE LISTING

<160> NUMBER OF SEQ ID NOS: 5

<210> SEQ ID NO 1
<211> LENGTH: 1231
<212> TYPE: DNA
<213> ORGANISM: Medicago sativa

<400> SEQUENCE: 1

```
ccaaatttca tttgaaaaaa aaaaatggct tcatcaatta atggccgaaa accaagtgaa      60
attttcaaag cacaagcttt attatacaaa catatatatg ccttcataga ttccatgtct     120
cttaaatggg ctgttgaaat gaacatacca aacataatcc aaaaccatgg caaaccaatt     180
tctctttcaa acttagtttc aattcttcaa gttccatcgt cgaaaatagg taacgtgcgg     240
cgtctcatgc gttacctcgc gcacaacgga ttcttcgaga taattacaaa agaagaagag     300
tcttatgctc tcactgttgc ttcagagctt cttgttagag gcagtgatct ttgtttagca     360
ccaatggttg agtgtgttct tgatccaact ctttcgggtt cgtatcatga gctgaagaaa     420
tggatttatg aggaagatct tacactcttt ggtgttactt taggatctgg ttttttgggat    480 tttcttgata aaaatcctga atataatacc tcatttaatg atgcaatggc tagtgattct     540
aaattgataa acttggcatt gagagattgt gattttgtgt ttgatggatt ggaatcaatt     600
gtggatgttg gtggtggaac tggaacaact gctaagatta tttgtgagac tttccctaag    660
ttgaaatgta ttgtgtttga taggccacaa gttgtagaga acttatctgg aagcaataat    720
ttgacttatg ttggtgggga catgttcaca tctattccta atgctgatgc agttttgctt    780
aagtatattc tacataattg gactgataag gattgcctaa ggatactgaa gaaatgtaaa    840
gaagctgtta caaatgatgg gaaaagagga aaagtgacta ttatagacat ggtgatagat    900
aaaaaaaaag atgagaatca agttactcaa attaagctcc ttatggatgt aaacatggct    960
tgtctaaatg gaaaagagag aaatgaggaa gaatggaaga aactcttcat agaagctggt   1020
ttccaacact ataagatatc tcctttgact ggattttttgt ctcttattga gatctatcca   1080
taaacacttt tgctttgatc attcatccat tctattgttt catgttataa accaatcttg   1140
ttctctatta tgatatctca cttgtaatat gcatttgttg gtaacaaata atagaatttg   1200
catacatgta tgattttttaa aaaaaaaaa a                                    1231
```

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 2

```
gggtacctgg atagatctca ataagaga                                      28

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 3
cgcggatcca tggcttcatc aattaatgg                                     29

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 4
ggccatatgg cttcatcaat tatggc                                        26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 5
cgggatcctt atggatagat ctcaa                                         25
```

ISOFLAVONOID METHYLATION ENZYME

This application is a divisional of application Ser. No. 09/926,571 filed Nov. 28, 2001, now U.S. Pat. No. 6,878,859 which is a national stage application under 35 U.S.C. §371 of International Application No. PCT/US00/13389 filed May 15, 2000, which claims priority to U.S. Provisional Application Ser. No. 60/135,026 filed May 20, 1999, the entire contents of which are hereby incorporated by reference.

TECHNICAL FIELD OF THE INVENTION

The invention relates to gene manipulation in plants.

BACKGROUND OF THE INVENTION

The isoflavonoids of the *Leguminosae* are among the most important biologically active classes of phenylpropanoid-derived plant natural products. Isoflavones such as daidzein, genistein and biochanin A exhibit a wide range of pharmacological effects including estrogenic, antiangiogenic, antioxidant and anticancer activities (Dixon, R. A. 1999. "Isoflavonoids: biochemistry, molecular biology and biological functions." In U. Sankawa, eds, *Comprehensive Natural Products Chemistry*, Elsevier, pp 773-823), and the health promoting activity of high soy diets are believed to reside in their isoflavone components (Barnes, et al. 1990. "Soybeans inhibit mammary tumors in models of breast cancer." In M. W. Pariza, eds, *Mutagens and Carcinogens in the Diet*, Wiley-Liss, Inc, New York, pp 239-253; Adlercreutz, et al. 1991. "Urinary excretion of lignans and isoflavonoid phytoestrogens in Japanese men and women consuming a traditional Japanese diet," *Am J Clin Nutr* 54: 1093-1100; Lee, et al. 1991. "Dietary effects on breast-cancer risk in Singapore," *Lancet* 337: 1197-1200). Daidzein and genistein act as precursors in the biosynthesis of various antimicrobial isoflavonoid phytoalexins in a wide variety of legumes (Dixon, R. A. and N. L. Paiva 1995. "Stress-induced phenylpropanoid metabolism," *Plant Cell* 7: 1085-1097). Furthermore, due to their estrogenic activity, high levels of isoflavonoids such as the phytoestrogen formononetin can adversely affect the reproductive capacity of sheep grazing forage legumes (Shutt, D. A. 1976. "The effects of plant oestrogens on animal reproduction," *Endeavour* 75: 110-113).

Isoflavonoids have been ascribed key roles in plant-pathogen interactions because many have quite strong antimicrobial activity. Antimicrobial isoflavonoids fall into two functional classes, the pre-formed "phytoanticipins" and the inducible "phytoalexins" (VanEtten, et al. 1994. "Two classes of plant antibiotics: phytoalexins versus phytoanticipins," *The Plant Cell* 6: 1191-1192). Examples of the former class include the prenylated isoflavones of lupin, which are synthesized in various organs of the plant during seedling development (Ingham, et al. 1983. "Fungitoxic isoflavones from *Lupinus albus* and other *Lupinus* species," *Zeitschrift für Naturforschung*, C 38: 194-200). Examples of the latter include several pterocarpans, the biosynthesis of which has been studied in detail, particularly in the cases of phaseollin, medicarpin, pisatin and glyceollin from bean, alfalfa, pea and soybean, respectively (Dixon, R. A. 1999. "Isoflavonoids: biochemistry, molecular biology and biological functions," *Comprehensive Natural Products Chemistry*, Vol. 1, U. Sankawa, ed, Elsevier, pp. 773-823).

Isoflavonoid compounds have been shown to accumulate in infected plant cells to levels known to be antimicrobial in vitro. The temporal, spatial and quantitative aspects of accumulation are consistent with a role for these compounds in disease resistance (Rahe, J. E. 1973. "Occurrence and levels of the phytoalexin phaseollin in relation to delimitation at sites of infection of *Phaseolus vulgaris* by *Colletotrichum lindemuthianum*," *Can J Botany* 51: 2423-2430; Hadwiger, L. A. and D. M. Webster. 1984. "Phytoalexin production in five cultivars of pea differentially resistant to three races of *Pseudomonas syringae* pv. *Pisi*," *Phytopathology* 74: 1312-1314; Long, et. al. 1985. "Further studies on the relationship between glyceollin accumulation and the resistance of soybean leaves to *Pseudomonas syringae* pv. *Glycinea*," *Phytopathology* 75: 235-239; Bhattacharyya, M. K. and E. W. Ward. 1987. "Biosynthesis and metabolism of glyceollin I in soybean hypocotyls following wounding or inoculation with *Phytophthora megasperma* f. sp. *Glycinea*," *Physiol Mol Plant Pathol* 31: 387405). Inhibition of the synthesis of glyceollin by application of an inhibitor of L-phenylalanine ammonia-lyase (PAL) to soybean seedlings breaks resistance to *Phytophthora megasperma* f. sp. *glycinea* (Moesta, P. and H. Grisebach. 1982. "L-2-Aminooxy-3-phenylpropionic acid inhibits phytoalexin accumulation in soybean with concomitant loss of resistance against *Phytophthora megasperma* f. sp. *Glycinea*," *Physiol Plant Pathol* 21: 65-70). Isolates of the fungal pathogen *Nectria hematococca* with reduced ability to degrade the pea phytoalexin pisatin have reduced virulence on pea, suggesting that pisatin is functionally involved in the disease resistance response (Kistler, H. C. and H. D. VanEtten. 1984. "Regulation of pisatin demethylation in *Nectria haematococca* and its influence on pisatin tolerance and virulence," *J Gen Micro* 130: 2605-2613).

Phytoalexins accumulate more rapidly, and to higher levels, during resistant interactions between a plant and its microbial pathogens than during susceptible interactions that result in disease (Dixon, R. A., and M. J. Harrison. 1990. "Activation, structure and organization of genes involved in microbial defense in plants," *Adv Genet* 28: 165-234). Therefore, increasing the rate at which phytoalexins accumulate, and the absolute levels attained, would result in increased resistance (Lamb, et al. 1992. "Emerging strategies for enhancing crop resistance to microbial pathogens," *Bio/technology* 10: 1436-1445).

Certain methylated forms of isoflavones, for example formononetin (7-hydroxy-4'-methoxyisoflavone) and biochanin A (5,7-dihydroxy-4'-methoxyisoflavone) have been shown to provide a nutraceutical benefit. For example, biochanin A and formononetin are reported to be phytoestrogens, and biochanin A has been shown to be effective in animal cancer study models. (Yangihara, et al. 1993. "Antiproliferative effects of isoflavones on human cancer cell lines established from the gastrointestinal tract," *Cancer Res* 53: 5815-5821; and Zhou-Jin-Rong, et al. 1998. "Inhibition of murine bladder tumorigenesis by soy isoflavones via alterations in the cell cycle, apoptosis, and angiogenesis," *Cancer Res* 58: 5231-5238).

As seen from the above examples, genetic manipulation of isoflavonoid biosynthesis in transgenic plants would positively impact plant, animal and human health (Dixon, et al. 1999. "Molecular controls for isoflavonoid biosynthesis in relation to plant and human health," *Recent Advances in Phytochemistry* 33: 133-160). However, the enzymes responsible for increasing isoflavonoid phytoalexin accumulation have not been identified, and not all the genes encoding the enzymes of isoflavonoid phytoalexin biosynthesis have been cloned.

The biosynthetic branch pathway leading to isoflavones in plants involves a cytochrome P450 mediated 2-hydroxylation/aryl migration of a flavanone intermediate formed from phenylpropanoid- and acetate-derived precursors via the chalcone synthase and chalcone isomerase reactions (FIG. 1)

(Kochs, G. and H. Grisebach. 1986. "Enzymic synthesis of isoflavones," *Eur J Biochem* 155: 311-318; Hakmatsuka, et al. 1991. "P450-dependent oxidative rearrangement in isoflavone biosynthesis: reconstitution of P-450 and NADPH:P450 reductase", *Tetrahedron* 47: 5969-5978; Steele, et al. 1999. "Molecular characterization of the enzyme catalyzing the aryl migration reaction of isoflavonoid biosynthesis in soybean," *Arch Biochem Biophys* 367: 146-150; and Jung, et al. 2000. "Identification and expression of isoflavone synthase: the key enzyme for biosynthesis of isoflavones in legumes," *Nature Biotechnology* 18: 208-212). After aryl migration, the 2-hydroxy isoflavanone intermediate undergoes dehydration to yield the corresponding isoflavone (Hakamatsuka, et al. 1998. "Purification of 2-hydroxyisoflavanone dehydratase from the cell cultures of *Pueraria lobata*," *Phytochemistry* 49: 497-505). Genistein (4', 5, 7-trihydroxyisoflavone) is the product of aryl migration/dehydration of naringenin (4', 5, 7-trihydroxyflavanone), whereas daidzein (4', 7-dihydroxyisoflavone) is formed in a similar manner from liquiritigenin (4', 7-dihydroxyflavanone). 4'-O-Methylation of daidzein yields formononetin (7-hydroxy-4'-methoxyisoflavone), whereas 4'-O-methylation of genistein yields biochanin A (5,7-dihydroxy-4'-methoxyisoflavone), an important anticancer compound found in chickpea (Yanagihara, et al. 1993. "Antiproliferative effects of isoflavones on human cancer cell lines established from the gastrointestinal tract," *Cancer Res* 53: 5815-5821) (FIG. 1).

In alfalfa and certain other legumes such as chickpea, methylation of the 4'-hydroxyl is a prerequisite for further substitutions of the isoflavonoid nucleus leading to pterocarpan phytoalexins such as medicarpin (Dixon, R. A. 1999. "Isoflavonoids: biochemistry, molecular biology and biological functions," In U. Sankawa, eds, *Comprehensive Natural Products Chemistry*, Elsevier, pp 773-823). This reaction is important biotechnologically, because it represents a pathway entry point for conversion of isoflavones with human anticancer activity into downstream metabolites with antifungal activity for the plant. However, the exact mechanism of this O-methylation reaction has remained unclear. Based on radiolabeling studies in copper-induced alfalfa seedlings in which formononetin, but surprisingly not daidzein, was incorporated into the pterocarpan medicarpin, it has been proposed that the 4'-O-methylation might be an integral part of the aryl migration reaction of isoflavone biosynthesis (Dewick, P. M. and M. Martin. 1979. "Biosynthesis of pterocarpan, isoflavan and coumestan metabolites of *Medicago sativa*: chalcone, isoflavone and isoflavanone precursors," *Phytochemistry* 18: 597-602). However, aryl migration occurs in vitro in the absence of methylation (Kochs, G. and H. Grisebach. 1986. *Eur J Biochem* 155: 311-318; Hakamatsuka, et al. 1991. *Tetrahedron* 47: 5969-5978; Kessmann, et al. 1990. "Stress responses in alfalfa (*Medicago sativa* L.) III. Induction of medicarpin and cytochrome P450 enzyme activities in elicitor-treated cell suspension cultures and protoplasts," *Plant Cell Rep* 9: 3841; Steele, et al. 1999. "Molecular characterization of the enzyme catalyzing the aryl migration reaction of isoflavonoid biosynthesis in soybean," *Arch Biochem Biophys* 367: 146-150), and mutants of subterranean clover exist in which formononetin and biochanin A are virtually absent, and daidzein and genistein accumulate instead (Wong, E. and C. M. Francis. 1968. "Flavonoids in genotypes of *Trifolium subterraneum*-II. Mutants of the Geraldton variety," *Phytochemistry* 7: 2131-2137), indicating that the isoflavones are the natural substrates for 4'-O-methylation. The problem has also been compounded by the fact that it has not proven possible to purify a S-adenosyl-L-methionine (SAM) dependent O-methyltransferase (OMT) that can catalyze 4'-O-methylation of daidzein. Instead, the SAM-dependent isoflavone OMT from alfalfa (He, X-Z and R. A. Dixon. 1996. "Affinity chromatography, substrate/product specificity and amino acid sequence analysis of an isoflavone O-methyltransferase from alfalfa (*Medicago sativa* L.),"*Arch Biochem Biophys* 336: 121-129) produces 7-O-methyldaidzein (isoformononetin) in vitro by methylation of the hydroxyl group at the 7-position. Isoformononetin is a rarely occurring plant natural product that has not been reported from alfalfa.

The isoflavone 7-OMT has been cloned from alfalfa and the recombinant enzyme converts daidzein exclusively to isoformononetin when expressed in *E. coli* (He, et al. 1998. "Stress responses in alfalfa (*Medicago sativa* L.) XXII. cDNA cloning and characterization of an elicitor-inducible isoflavone 7-O-methyltransferase," *Plant Mol Biol* 36: 43-54). This enzyme activity, and its corresponding transcripts, are strongly induced in elicited alfalfa cell cultures coordinately with other enzymes of medicarpin biosynthesis (Dalkin, et al. 1990. "Stress responses in alfalfa (*Medicago sativa* L.) I. Elicitor-induction of phenylpropanoid biosynthesis and hydrolytic enzymes in cell suspension cultures," *Plant Physiol* 92: 440-446; He, et al. 1998. *Plant Mol Biol* 36: 43-54).

A large number of plant OMT sequences are now available in the databases, most of which encode enzymes that act on hydroxycinnamic acid intermediates of lignin biosynthesis or on flavonoid derivatives (Ibrahim, et al. 1998. "Plant O-methyltransferases: molecular analysis, common signature and classification," *Plant Mol Biol* 36: 1-10; Joshi, C. P. and V. L. Chiang. 1998. "Conserved sequence motifs in plant S-adenosyl-L-methionine-dependent methyltransferases," *Plant Mol Biol* 37: 663-674). In nearly all cases, the enzymes exhibit strict regiospecificity; for example, a series of distinct, position-specific OMTs is involved in the synthesis of polymethylated flavonols in *Chrysosplenium americanum* (Ibrahim, et al. 1987. "Enzymology and compartmentation of polymethylated flavonol glucosides in *Chrysosplenium americanum*," *Phytochemistry* 26: 1237-1245; Gauthier, et al. 1996. "cDNA cloning and characterization of a 3'/5'-O-methyltransferase for partially methylated flavonols from *Chrysosplenium americanum*," *Plant Mol Biol* 32: 1163-1169). However, some OMTs appear to be more versatile, acting on both flavonoids and hydroxycinnamic acids (Gauthier, et al. 1998. "Characterization of two cDNA clones which encode O-methyltransferases for the methylation of both flavonoid and phenylpropanoid compounds," *Arch Biochem Biophys* 351: 243-249), or are specific for more than one related substrate, such as the well-studied caffeic acid/5-hydroxyferulic acid OMTs of lignin biosynthesis (Bugos, et al. 1991. "cDNA cloning, sequence analysis and seasonal expression of lignin-bispecific caffeic acid/5-hydroxyferulic acid O-methyltransferase of aspen," *Plant Mol Biol* 17: 1203-1215; Li, et al. 2000. "5-Hydroxyconiferyl aldehyde modulates enzymatic methylation for syringyl monolignol formation, a new view of monolignol biosynthesis in angiosperms," *J Biol Chem* 275: 6537-6545). However, there have been no reports of OMTs, or any other plant natural product biosynthetic enzymes, that exhibit different regiospecificity in vivo and in vitro.

Utilizing the different regiospecificity of isoflavone 7-OMT in vivo, it is now possible to genetically manipulate biologically active 4'-O-methylated isoflavonoids.

SUMMARY OF THE INVENTION

In one aspect the invention is a method for increasing the level of at least one 4'-O-methylated isoflavonoid compound in a target plant comprising transforming the target plant with a DNA fragment comprising an isoflavone O-methyltransferase gene to form a transgenic plant and over-expressing the isoflavone O-methyltransferase gene in the transgenic plant under the control of a suitable constitutive or inducible promoter. In particular, the 4'-O-methylated isoflavonoid compound can be a 4'-O-methylated isoflavonoid phytoalexin or a 4'-O-methylated isoflavonoid nutraceutical. In a preferred embodiment, the DNA fragment used to transform the plant comprises SEQ ID NO:1 or a sequence exhibiting at least moderate hybridization with SEQ ID NO:1.

In another aspect, the invention is a method for producing at least one 4'-O-methylated isoflavonoid compound in a target plant that does not produce the 4'-O-methylated isoflavonoid compound comprising transforming the target plant with a DNA fragment comprising an isoflavone O-methyltransferase gene to form a transgenic plant and expressing said isoflavone O-methyltransferase gene in said transgenic plant under the control of a suitable constitutive or inducible promoter, wherein the transgenic plant contains all the other necessary enzymes of isoflavonoid biosynthesis to produce the 4'-O-methylated isoflavonoid compound. In particular, the 4'-O-methylated isoflavonoid compound can be a 4'-O-methylated isoflavonoid phytoalexin or a 4'-O-methylated isoflavonoid nutraceutical. The target plant can possess native DNA encoding the other necessary enzymes for isoflavonoid biosynthesis. Alternatively, if the target plant lacks a necessary enzyme, it can be transformed with a DNA fragment encoding the deficient enzyme. In a preferred embodiment, the DNA fragment used to transform the plant comprises SEQ ID NO:1 or a sequence exhibiting at least moderate hybridization with SEQ ID NO:1.

In another aspect, the invention is a method for producing at least one 4'-O-methylated isoflavonoid nutraceutical in non-plant cell system by expression of a DNA fragment comprising an isoflavone O-methyltransferase gene under the control of a suitable constitutive or inducible promoter in cells that have been genetically transformed to contain all the other necessary enzymes of isoflavonoid biosynthesis to make the 4'-O-methylated isoflavonoid nutraceutical. In a preferred embodiment, the DNA fragment used to transform the plant comprises SEQ ID NO:1 or a sequence exhibiting at least moderate hybridization with SEQ ID NO:1.

In another aspect, the invention is a method for decreasing the levels of formononetin, at least one of its conjugates or mixtures thereof in a transgenic forage legume such as alfalfa comprising antisense expression or sense gene-mediated silencing using a DNA fragment comprising an isoflavone O-methyltransferase gene under the control of a suitable constitutive or inducible promoter. Alternatively, the isoflavone O-methyltransferase could be down-regulated by nucleic acid-mediated insertional inactivation. In a preferred embodiment, the DNA fragment used to transform the plant comprises SEQ ID NO:1 or a sequence exhibiting at least moderate hybridization with SEQ ID NO:1.

In another aspect, the invention is a method for decreasing the levels of at least one 4'-O-methylated isoflavonoid compound in a target plant having all the necessary enzymes for synthesizing said 4'-O-methylated isoflavonoid compound comprising transforming the target plant with a DNA fragment comprising an isoflavone O-methyltransferase gene to form a transgenic plant and inducing antisense expression, sense gene-mediated silencing, or nucleic acid-mediated insertional inactivation of the isoflavone O-methyltransferase gene under the control of a suitable constitutive or inducible promoter. This method is useful for decreasing compounds selected from the group consisting of a 4'-O-methylated isoflavonoid phytoalexin, a 4'-O-methylated isoflavonoid phytoalexin conjugate and mixtures thereof. In a preferred embodiment, the DNA fragment used to transform the plant comprises SEQ ID NO:1 or a sequence exhibiting at least moderate hybridization with SEQ ID NO:1.

In another aspect, the invention is a method for decreasing the level of at least one 4'-O-methylated isoflavonoid nutraceutical, at least one 4'-O-methylated isoflavonoid nutraceutical conjugate or mixtures thereof in a target plant having all the necessary enzymes for synthesizing the 4'-O-methylated isoflavonoid nutraceutical or conjugate comprising transforming the target plant with a DNA fragment comprising an isoflavone O-methyltransferase gene to form a transgenic plant and inducing antisense expression or sense gene-mediated silencing of the isoflavone O-methyltransferase gene under the control of a suitable constitutive or inducible promoter, thereby increasing the level of the corresponding non-methylated precursor, its conjugate or mixture thereof. In a preferred embodiment, the DNA fragment used to transform the plant comprises SEQ ID NO:1 or a sequence exhibiting at least moderate hybridization with SEQ ID NO:1.

In another aspect, the invention is a method for the production of a 7-O-methylated isoflavonoid compound comprising contacting intact plants or cell suspension cultures with a non-methylated isoflavone precursor of the 7-O-methylated isoflavonoid compound, with the intact plants or cell suspension cultures transformed with a DNA fragment comprising an isoflavone O-methyltransferase gene under the control of a suitable constitutive or inducible promoter. In a preferred embodiment, the DNA fragment used to transform the plant comprises SEQ ID NO:1 or a sequence exhibiting at least moderate hybridization with SEQ ID NO:1.

In another aspect, the invention is a method for the production of a 7-O-methylated isoflavonoid compounds comprising contacting a soluble or immobilized isoflavone O-methyltransferase enzyme with a non-methylated isoflavone precursor to the 7-O-methylated isoflavonoid compound, wherein the enzyme is produced by expression of a DNA fragment comprising the corresponding isoflavone O-methyltransferase gene in transgenic plants or a heterologous system. In a preferred embodiment, the heterologous system is selected from the group consisting of transfected bacterial, yeast and insect cells. In a preferred embodiment, the DNA fragment used to transform the plant comprises SEQ ID NO:1 or a sequence exhibiting at least moderate hybridization with SEQ ID NO:1.

In yet another aspect, the invention is an antiserum against 4'-O-methyltransferase used as a reagent for determining transgene expression of said 4'-O-methyltransferase in plants.

In yet another aspect, the invention is a method of increasing disease resistance in a target plant by transforming the target plant with a DNA fragment comprising an isoflavone O-methyltransferase gene, wherein the transformed plant exhibits increased levels of 4'-O-methylated isoflavonoids when compared to levels of 4'-O-methylated isoflavonoids in plants of the same species which do not comprise the DNA fragment. In a preferred embodiment, the DNA fragment used to transform the plant comprises SEQ ID NO:1 or a sequence exhibiting at least moderate hybridization with SEQ ID NO:1.

In yet another aspect, the invention is a composition comprising at least one 4'-O-methylated isoflavonoid suitable for administration as a food stuff, a nutritional supplement, an animal feed supplement, a nutraceutical, or a pharmaceutical, wherein the 4'-O-methylated isoflavonoid is isolated from at least a portion of a transgenic plant transformed with a DNA fragment comprising an isoflavone O-methyltransferase gene and wherein the transgenic plant exhibits increased levels of 4'-O-methylated isoflavonoids when compared to levels of 4'-O-methylated isoflavonoids in plants of the same species which do not comprise the DNA fragment. In a preferred embodiment, the DNA fragment used to transform the plant comprises SEQ ID NO:1 or a sequence exhibiting at least moderate hybridization with SEQ ID NO:1. An exemplary plant is a legume.

In another aspect, the invention is a transgenic plant comprising at least one recombinant DNA sequence encoding a portion of an isoflavone O-methyltransferase gene, wherein the plant upon expression of the gene exhibits increased levels of 4'-O-methylated isoflavonoid compounds when compared to levels of 4'-O-methylated isoflavonoid compounds in plants of the same species which do not comprise the recombinant DNA sequence. The invention also includes seed, progeny, and progeny from the seed from this transgenic plant.

In another aspect, the invention is a transgenic plant comprising at least one recombinant DNA sequence encoding a portion of an isoflavone O-methyltransferase gene, wherein the plant upon expression of the gene exhibits decreased levels of 4'-O-methylated isoflavonoid compounds when compared to levels of 4'-O-methylated isoflavonoid compounds in plants of the same species which do not comprise the recombinant DNA sequence. The invention also includes seed, progeny, and progeny from the seed from this transgenic plant.

BRIEF DESCRIPTION OF THE DRAWINGS

FIG. 2 depicts the nucleotide sequence for the alfalfa isoflavone 4'-O-methyl transferase (IOMT)8 cDNA (SEQ ID NO:1).

FIG. 3A-3B depicts generation and molecular analysis of transgenic alfalfa altered in expression of IOMT. FIG. 3A depicts the binary vector constructs harboring IOMT sequences in sense and antisense orientations. FIG. 3B depicts enzymatic activity of IOMT in leaf tissue from untransformed "C" and empty vector transformed "V" controls, and a range of IOMT8 sense transformants.

FIGS. 4A and 4B depict high pressure liquid chromatography (HPLC) profiles of phenolic compounds from leaves of empty vector control plant #62C and IOMT sense transgenic line #69 24 hr after infiltration with Pi buffer, respectively. FIGS. 4C and 4D depict HPLC profiles of leaf extracts from the same vector control and sense transgenic lines, respectively, 24 hr after feeding daidzein in Pi buffer by leaf infiltration.

FIGS. 5A and 5B are HPLC profiles of leaf extracts from $CuCl_2$-treated plants of vector control line #9C and IOMT over-expressing line #67, respectively, 32 hr after exposure to 3 mM $CuCl_2$. Peaks labeled 1-4 were identified as apigenin conjugate, 7,4'-dihydroxyflavone, 7,4'-dihydroxyflavanone and apigenin aglycone, respectively. FIGS. 5C and 5D are HPLC profiles of leaf extracts from plants of vector control line #9C and IOMT over-expressing line #67, respectively, 32 hr after transfer of seedlings to water. FIGS. 5E and 5G depict levels of formononetin and FIGS. 5F and 5H depict levels of medicarpin in leaves of replicate vegetatively propagated vector control lines #9C and #62C (control lines) and IOMT over-expressing lines #67 and #69, 32 hr after exposure to $H_2O$ or 3 mM $CuCl_2$.

FIGS. 6A and 6B are HPLC profiles of extracts from *Phoma medicaginis* infected leaves of empty vector control line #64C and IOMT over-expressing line #67, respectively at 12 hr post-inoculation. FIGS. 6C and 6D are HPLC profiles of extracts from uninoculated leaves of line #64C and #67, respectively. FIGS. 6E and 6F depict levels of formononetin glucoside or medicarpin, respectively, in leaves of replicate vegetatively propagated vector control (line #64C) and IOMT over-expressing (lines #67 and #69) plants at various times after inoculation with *P. medicaginis*.

FIG. 8A depicts sizes of 100 individual lesions on leaves of empty vector control line #64C and IOMT over-expressing line #69, measured 5 days post-inoculation. The average value for the size of the wounds produced by the tracing wheel alone for a parallel series of 100 wound sites has been subtracted. The solid lines show the means for the control lines and the dashed lines show the means for the IOMT over-expressing lines. The bars show the standard deviations. FIG. 8B depicts sizes of 100 individual lesions on leaves measured 5 days post-inoculation as described above, but showing lesions on IOMT over-expressing line #67 and the empty vector control line #64C infected in parallel.

DETAILED DESCRIPTION

By using reverse genetic and ectopic expression approaches in transgenic alfalfa, it has now been found that the alfalfa isoflavone OMT is involved in the formation of a different product in vivo (formononetin) compared to in vitro (isoformononetin). Because of the in vivo regiospecificity of the alfalfa isoflavone OMT, the levels of formononetin in transgenic plants can now be genetically manipulated for the purpose of reducing levels of this compound and thereby improving forage quality. In another embodiment, transgenic reduction of isoflavone 4'-O-methylation can also be used to increase the levels of the immediate precursors of this reaction, daidzein and genistein, which are important nutraceuticals. It is shown herein that isoflavone OMT functions operationally as a rate-limiting enzyme for production of the antimicrobial phytoalexin medicarpin in infected alfalfa leaves, such that over-expression of isoflavone OMT in transgenic alfalfa causes a significant increase in the levels of medicarpin following infection by a pathogenic fungus, leading to strongly increased disease resistance. The functional identification of the alfalfa IOMT has now made possible methods for increasing or decreasing the levels of formononetin or other 4'-O-methylated isoflavonoid nutraceuticals such as biochanin A, texasin, afrormosin, and pseudobaptigenin in plants that produce these compounds, and for increasing the levels of medicarpin or related 4'-O-methylated isoflavonoid phytoalexins such as maackiain or pisatin and thereby improving disease resistance. Thus, transgenic expression of isoflavone OMT in legumes can be used to engineer both phytoalexin levels for improved disease resistance and health promoting nutraceutical phytochemicals. Furthermore, IOMT can also be used to engineer isoflavone 4'-O-methylation in plants, or other organisms, that do not naturally produce isoflavonoids, but have been engineered to do so by introduction of the necessary isoflavone synthase.

Figure 1:
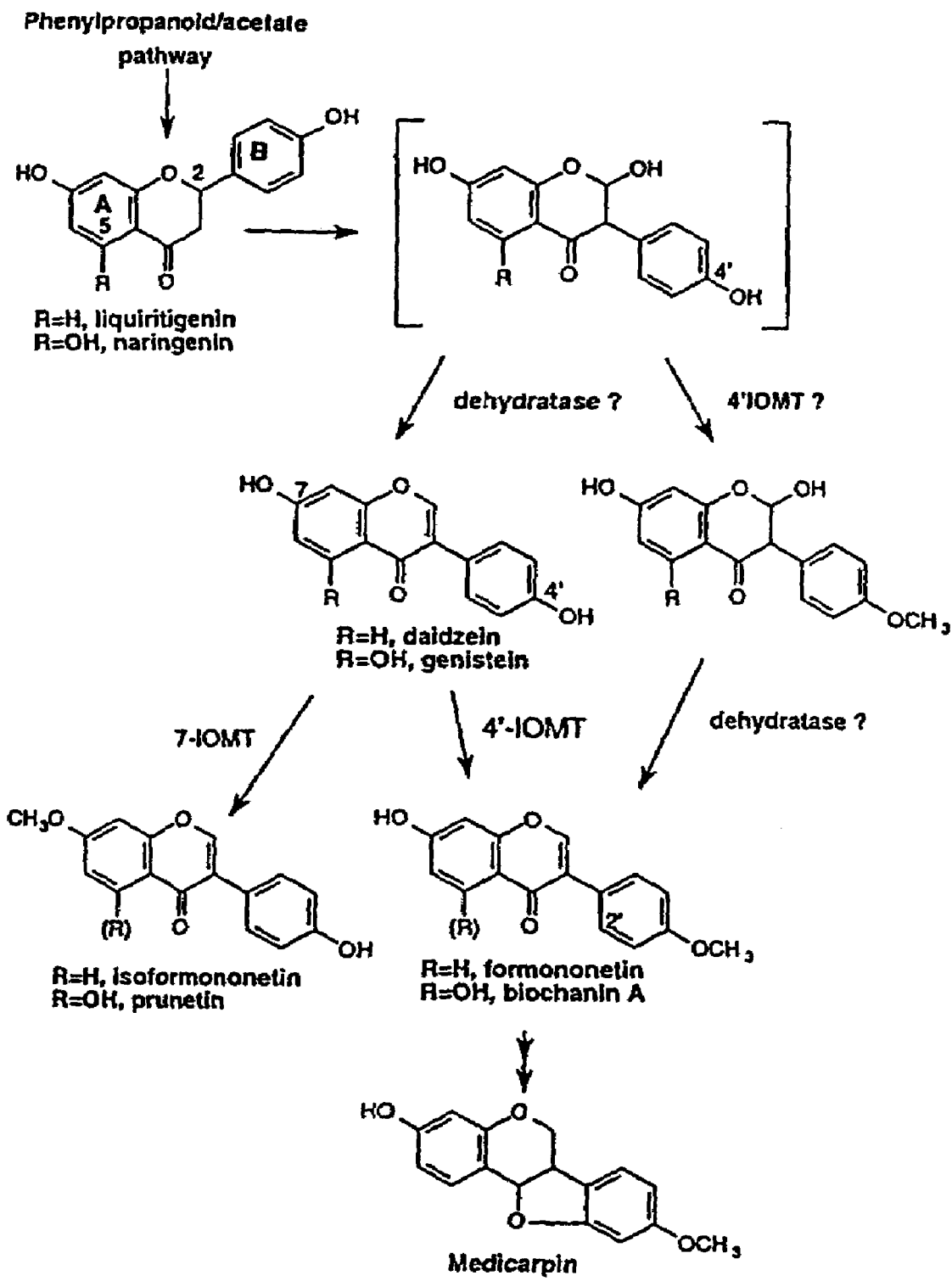
FIG. 1 depicts pathways for the formation and O-methylation of isoflavones in plants. The flavanones naringenin and liquiritigenin are formed by the action of chalcone synthase and chalcone isomerase, with loss of the 5-hydroxyl in liquiritigenin occurring by co-action of chalcone reductase with chalcone synthase. Aryl migration of the B-ring is catalyzed by 2-hydroxyisoflavanone synthase leading, after dehydration, to daidzein or genistein. Conversion of formononetin to medicarpin proceeds via 2'-hydroxylation, reduction and ring closure steps (Dixon, R. A. 1999. In U. Sankawa, ed, *Comprehensive Natural Products Chemistry*, Elsevier, pp 773-823).

To demonstrate that isoflavone O-methyltransferase (IOMT) is involved in the production in vivo of formononetin, and therefore medicarpin, which is derived from formononetin by the pathway shown in FIG. 1, transgenic alfalfa plants were made which either under- or over-expressed IOMT as follows.

EXAMPLE 1

Construction and Characterization of Expression Plasmids Containing Exemplary IOMT cDNA The full-length alfalfa IOMT8 cDNA (SEQ ID NO:1 and FIG. 2) was placed in the sense and antisense orientations under control of the cauliflower mosaic virus 35S promoter for constitutive expression in alfalfa. All recombinant DNA techniques were performed as described in Sambrook et al. (Sambrook, et al. 1989. *Molecular Cloning. A Laboratory Manual* (2nd Ed), Cold Spring Harbor Laboratory Press, New York). For sense vector construction, the expression plasmid pET15b/IOMT8, which contains the full-length IOMT8 cDNA (He, et al. 1998. *Plant Mol Biol* 36: 43-54), was digested with BamHI and NcoI. A 1.2 Kb fragment was isolated and subcloned into the NcoI and BamHI sites of plasmid pRTL2 (Restrepo, et al. 1990. "Nuclear transport of plant polyviral proteins," *Plant Cell* 2: 987-998): For antisense vector construction, the full length IOMT8 cDNA was amplified by polymerase chain reaction (PCR) using the following primers: 5'-GGGTACCTGGATAGATCTCAATAA-GAGA-3' (SEQ ID NO:2) and 5'-CGCGGATCCATGGCT-TCATCAATTAATGG-3' (SEQ ID NO:3), with added Kpn1 and BamHI restriction sites, and the PCR product was digested with Kpn1 and BamHI prior to cloning into pRTL2. Plasmids containing IOMT sequences in pRTL2 were digested with HindIII, and 2.2 kb fragments containing the cauliflower mosaic virus 35S promoter, tobacco etch virus 5' untranslated leader sequence, IOMT sequence and CaMV terminator, were isolated and ligated into the HindIII site of the binary vector pGA482 (An, G. 1986. "Development of plant promoter expression vectors and their use for analysis of differential activity of nopaline synthase promoter in transformed tobacco cells," *Plant Physiol* 81: 86-91). The constructs were mobilized into *Agrobacterium tumefaciens* strain LBA4404 by electroporation (Cell-porator, GIBCO BRL, Gaithersburg, Md.). The gene constructs, utilizing the intermediate plasmid pRTL2 and the binary vector pGA482, are shown in FIG. 3A.

EXAMPLE 2

Genomic Insertion of IOMT Transgene by Transformation of Alfalfa

Alfalfa (*Medicago sativa* L. cv. Regen S Y) was transformed and regenerated through somatic embryogenesis using kanamycin (25 mg/L) as selectable marker (Thomas, et al. 1990. "Selection of interspecific somatic hybrids of *Medicago* by using *Agrobacterium*-transformed tissue," *Plant Sci* 69: 189-198). Trifoliate leaves were surface-sterilized for 10 sec in 70% ethanol and for 15 min in 1% (v/v) sodium hypochlorite solution containing 0.1% Tween 20 and then immersed for 10-15 min in a suspension of *Agrobacterium* LBA4404 harboring the IOMT constructs or empty vector (control). After rinsing with distilled water, tissues were blotted on a paper towel and plated on MS medium (Murashige, T. and Skoog, F. 1962. "A revised media for rapid growth and bioassay with tobacco tissue culture," *Physiol Plant* 15: 473-497) containing B5 vitamins, 0.25 g/l casein hydrolysate, 10 µM 2,4-dichlorophenoxyacetic acid (2,4-D), 5 µM 6-benzy-laminopurine (BAP), 0.1 mM acetosyringone, and 30 g/l sucrose (A1 medium). After 3 day co-cultivation, tissues were transferred to the above medium but containing 2 µM BAP, 500 µg/ml carbenicillin, 25 µg/ml kanamycin and no acetosyringone (A2 medium). Four weeks after subculture, calli were transferred to A2 medium with addition of 30 mM L-proline but no BAP (A3 medium) for embryo development. Somatic embryos were transferred to A3 medium without 2,4 D (A4 medium) for embryo germination. Seedlings that developed were finally transferred to A4 medium without casein hydrolysate and proline for rooting. Potted kanamycin-resistant plantlets were maintained in the greenhouse.

After plant regeneration via somatic embryogenesis as described above, transformants were analyzed by polymerase chain reaction (PCR) for genomic insertion of IOMT transgene sequences. Genomic DNA was extracted according to Edwards et. al. (Edwards, et al. 1991. "A simple and rapid method for the preparation of plant genomic DNA for PCR analysis," *Nucleic Acids Res* 19: 1359). Leaf tissues of transformants were extracted in 200 mM Tris-HCl, pH7.5, 250 mM NaCl, 25 mM ethylenediaminetetraacetic acid (EDTA), 0.5% sodium dodecyl sulfate (SDS), centrifuged for 5 min in a microfuge, and supernatants transferred to fresh Eppendorf tubes to which equal amounts of 2-propanol were added. After incubation for 2 min at room temperature, DNA was precipitated by centrifugation. Pellets were resuspended in 10 mM Tris-HCl, 1 mM EDTA, pH 8.0. PCR reactions were performed in 50 µl volumes containing 10 mM Tris-HCl pH 8.3, 50 mM KCl, 1.25 mM $MgCl_2$, 200 µM dNTPs, 0.5 units of Taq polymerase, 0.4 µM oligonucleotide primers and 200 ng of plant DNA. PCR amplification of IOMT sequences was performed with 5' (5'-GGCCATATGGCTTCATCAAT-TATGGC-3') (SEQ ID NO:4) and 3' (5'-CGGGATCCT-TATGGATAGATCTCAA-3') (SEQ ID NO:5) sequences of IOMT8 as primers. A Perkin Elmer Cetus 480 thermocycler was used for the amplification with 35 cycles of denaturation (94° C. for 1 min), annealing (55° C. for 1 min), and extension (72° C. for 1 min with a 5 min extension for the last cycle). Controls included DNA from empty vector transformed and non-transformed plants. More than 70% of the transformants contained the full length IOMT cDNA insert (data not shown). All the transgenic lines produced were phenotypically normal. Genomic integration of the transgene was confirmed in a subset of the transformants by Southern-blot analysis. To perform this, genomic DNA was isolated from leaf tissues (Edwards, et al. 1991. *Nucleic Acids Res* 19: 1359), digested with EcoRI or HindIII, subjected to electrophoresis through a 0.8% agarose gel and transferred to a Hybond-N membrane (Amersham, Piscataway, N.J.) by capillary blotting. The membrane was hybridized with $^{32}$P-labeled 800 bp IOMT probe (from nucleotide 249 to 1035 of SEQ ID NO:1 and FIG. 2) and washed in 0.2×SSC, 0.1% SDS at 42° C. for 20 min and 3 times for 30 min at 65° C. Sense transformants #52, #61, #62, #67, #69 and #78 had a higher transgene copy number than the other lines analyzed. Southern blot analysis following digestion with HindIII and hybridization with the T-DNA left border indicated that the individual transformants resulted from independent integration events.

EXAMPLE 3

Confirmation of IOMT Transgene by Use of Polyclonal Antiserum Against Alfalfa IOMT IOMT transcripts are not expressed in healthy alfalfa leaves (He, et al. 1998. *Plant Mol Biol* 36: 43-54), and therefore, demonstration of the presence of IOMT activity in leaves confirms the expression of the IOMT transgene. Leaf tissue extracts from representative sense transformants and vector control transgenic alfalfa plants were, therefore, subjected to western blot analysis, using a polyclonal antiserum against alfalfa IOMT expressed in *E. coli*, to assess levels of ectopic expression of the enzyme in leaves. Polyclonal antiserum against IOMT was produced by immunizing rabbits (Covance Research Products Inc., Denver, Pa.) with the protein antigen expressed from *E. coli* (He, et al. 1998. *Plant Mol Biol* 36: 43-54). Protein extracts from leaf tissues were solubilized in sample buffer (25 mM Tris-HCl, pH 6.8, 1% SDS, 2.5% 2-mercaptoethanol, 5% glycerol). Proteins were separated by SDS-PAGE and transferred to nitrocellulose membranes (Amersham, Piscataway, N.J.) by electrophoretic blotting in transfer buffer (25 mM Tris-HCl, pH 8.3, 150 mM glycine, 20% v/v methanol). Blots were probed using polyclonal antiserum against purified alfalfa IOMT as primary antibody, with anti-(rabbit IgG)-peroxidase conjugate as secondary antibody. The IOMT signal was detected by exposing the blots to X-ray film shortly after incubation with ECL reagent (Amersham, Piscataway, N.J.). While all of the sense transformants exhibited the presence of IOMT protein, Lines #67 and #69 exhibited the highest IOMT protein levels.

EXAMPLE 4

Effects of Trangenically Expressed IOMT

IOMT enzyme activity was measured in extracts from leaf tissues taken from plants maintained in the greenhouse. IOMT activity was analyzed as previously described (He, X-Z and R. A. Dixon. 1996. *Arch Biochem Biophys* 336: 121-129). Leaf tissues were ground into powder in liquid nitrogen, and extracted in enzyme assay buffer (200 mM Tris-HCl, pH 8.3, 5 mM EDTA, 14 mM 2-mercaptoethanol, 10% PVPP). After centrifugation, supernatants were used for enzyme activity assay. The reaction mixtures contained 100 mmol daidzein, 300 nmol S-[$^3$H-methyl] adenosyl-L-methionine and enzyme extract in a total volume of 120 µl. Reactions were carried out at 30° C. for 30 min and terminated by addition of 100 µL acetic acid. The reaction mixtures were extracted with 0.5 ml ethyl acetate, the ethyl acetate evaporated under $N_2$, and the residue resuspended in methanol. For product analysis, the re-suspended residue was applied to silica gel thin layer chromatography (TLC) plates (Si250; Baker, Philipsburg, N.J.). Following development in chloroform:methanol:triethylamine (8:1:1, v/v), the product of interest was scraped from the TLC plates and radioactivity quantified by liquid scintillation counting. For product analysis by HPLC, 20 µl of re-suspended residue was applied to a C18 column (5 µm particle size, 4.6 mm×250 mm) and eluted with a gradient of increasing solvent B in solvent A (solvent A, 1% phosphoric acid in water, solvent B, acetonitrile: 040 min, 20-45% B; 4042 min, 45-95% B). The eluate was monitored at 287 nm. Identity of products was confirmed by co-elution and diode array analysis of UV spectra with authentic samples of formononetin and isoformononetin.

Several independent transgenic lines harboring the IOMT sense construct expressed high IOMT activity (FIG. 3B). However, lines #62 and #78, with high transgene copy number, did not express IOMT activity. There was a direct relationship between the levels of IOMT protein determined by immunoblotting and the extractable activity of the enzyme from leaves. TLC and HPLC analysis of the labeled product formed from daidzein and S-[$^3$H-methyl] adenosyl-L-methionine showed that only isoformononetin was produced by the enzyme extracted from healthy, non-transformed alfalfa leaves (data not shown), consistent with the previously ascribed function of the enzyme as an isoflavone 7-O-methyltransferase.

Alfalfa roots accumulate formononetin malonyl glucoside (FMG), medicarpin, and medicarpin malonyl glycoside (MMG) (Sumner, et al. 1996. "High-performance liquid chromatography/continuous-flow liquid secondary ion mass spectrometry of flavonoid glucosides in leguminous plant extracts," *J Mass Spectrom* 31: 472-485). To determine whether down-regulation of IOMT affects the levels of these compounds in roots, extraction and HPLC analysis of phenolic compounds was performed as described previously (Dalkin, et al. 1990. *Plant Physiol* 92: 440-446). Equal amounts of tissue were ground in liquid $N_2$ and extracted twice with acetone overnight at room temperature. The extracts were centrifuged at 3,000 rpm for 30 min and the supernatants collected. The acetone was evaporated under $N_2$, and the residue dissolved in methanol. Insoluble material was removed by centrifugation at 12,000×g for 30 min. Twenty µl of the solution was applied to a C18 HPLC column (5 µm particle size, 4.6 mm×250 mm) and eluted with a gradient of increasing solvent B (solvent A, 1% phosphoric acid in water, solvent B, acetonitrile: 0-40 min, 20-45% B; 40-42 min, 45-95% B). The absorbance of the eluant was monitored at 287 nm. Retention times and calibration curves for formononetin, isoformononetin, medicarpin and conjugates were established with authentic samples. HPLC analysis of root extracts from greenhouse grown plants indicated that the levels of formononetin, FMG and MMG were highly variable, making it difficult to determine whether differences in metabolite levels were significant. Therefore, for analysis of antisense transgenic lines, plants selected initially on the basis of metabolite levels were vegetatively propagated and grown under growth chamber conditions. Three independent antisense lines #42, #54 and #60 exhibited significantly reduced levels of these compounds compared to the average values from a population of 46 independently propagated control plants, by 33% to 44% for FMG, by 29% to 71% for medicarpin and by 18% to 51% for MMG. The above results indicate that expression of IOMT antisense constructs reduces constitutive root isoflavone levels.

Figure 4A:
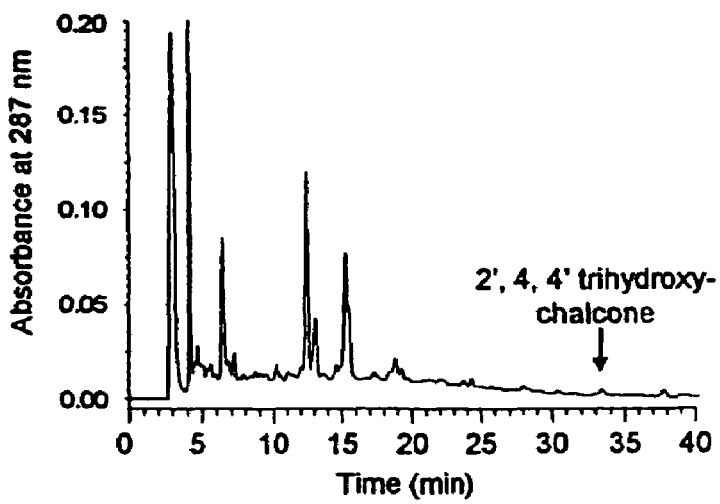
FIG. 4A-4D depicts the metabolism of daidzein after infiltration into untreated alfalfa leaves.
Figure 4B:
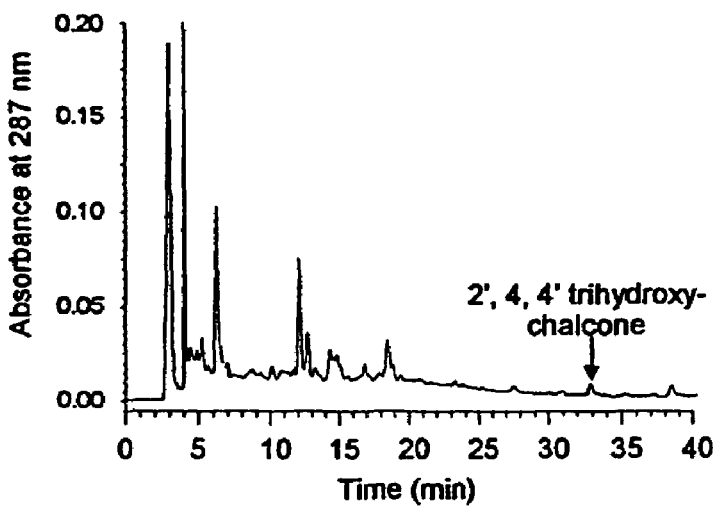
Figure 4C:
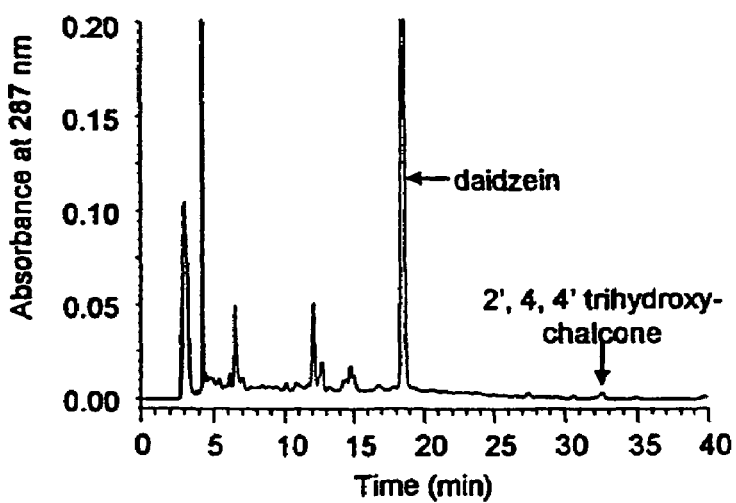
Figure 4D:
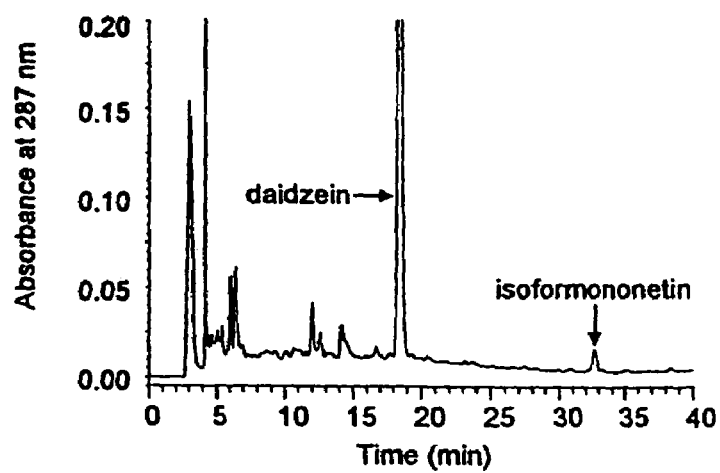
Figure 4E:
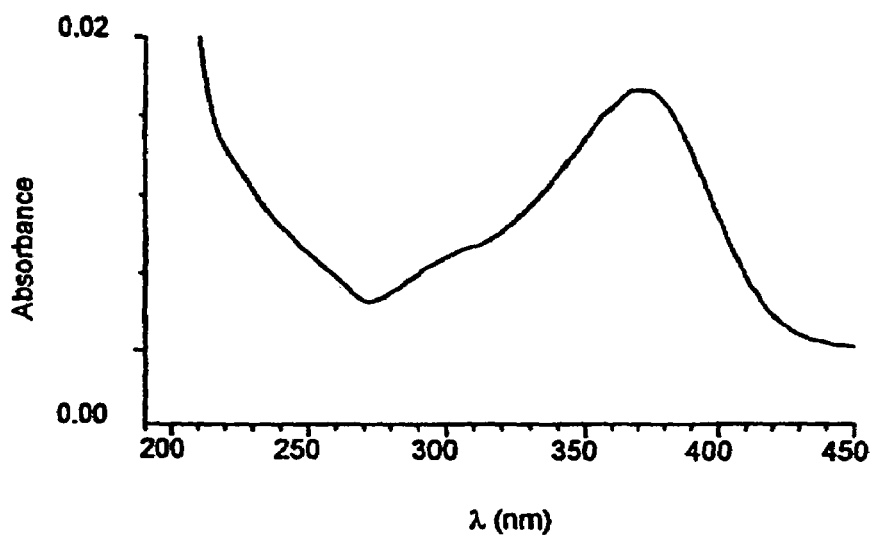
FIGS. 4E and 4F show UV spectra of 2', 4, 4'-trihydroxychalcone and isoformononetin, respectively.
Figure 4F:
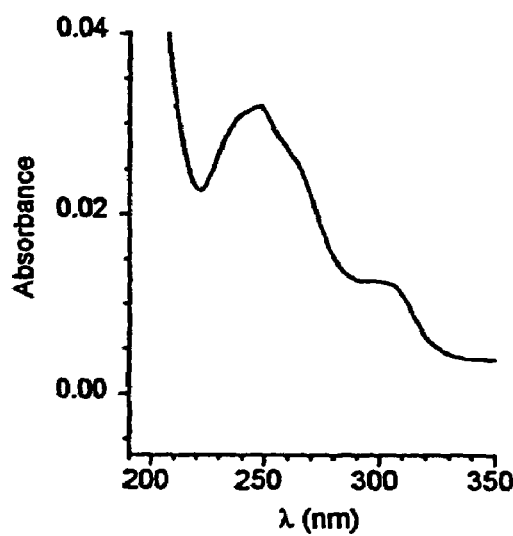

A number of independent alfalfa transformants with strong ectopic expression of IOMT in the leaves were analyzed for levels of constitutive isoflavonoid intermediates. The isoflavonoid pathway is only significantly expressed in alfalfa leaves following stress such as infection or elicitation (Higgins, V. J. 1972. "Role of the phytoalexin medicarpin in three leaf spot diseases of alfalfa," *Physiol Plant Pathol* 2: 289-300; Paiva, et al. 1994. "Regulation of isoflavonoid metabolism in alfalfa," *Plant Cell, Tissue and Organ Cult* 38: 213-220), and therefore, in the absence of induction of the enzymes that produce early isoflavonoid pathway substrates, the HPLC profiles of IOMT over-expressing and control leaves were identical (FIGS. 4A and 4B). No isoformononetin was detected. A minor compound running very close to the retention time of isoformononetin in extracts from Pi buffer treated leaves of control and IOMT over-expressing plants, and daidzein-fed leaves of control plants, was shown to be 2',4,4'-trihydroxychalcone, an intermediate of flavonoid biosynthesis (FIG. 4A-4C). However, isoformononetin was produced on feeding unlabeled daidzein to leaves of IOMT over-expressing transgenic alfalfa (FIG. 4D), whereas the daidzein remained unconverted when fed to leaves of control plants (FIG. 4C). Thus, the regiospecificity of IOMT in planta is identical to that displayed in vitro if the substrate is exogenously supplied to unstressed tissues, again consistent with the designation of the enzyme as an isoflavone 7-O-methyltransferase.

Figure 5A:
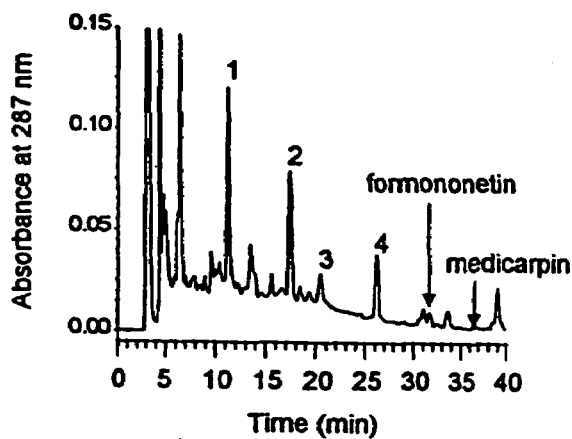
FIG. 5A-5H depict abiotic elicitation of isoflavonoid compounds in control and IOMT over-expressing transgenic alfalfa.
Figure 5B:
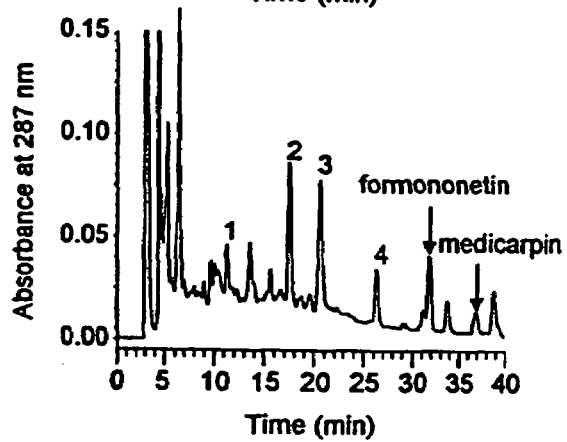
Figure 5C:
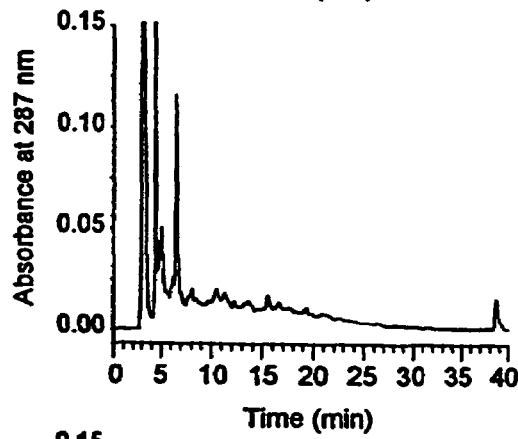
Figure 5D:
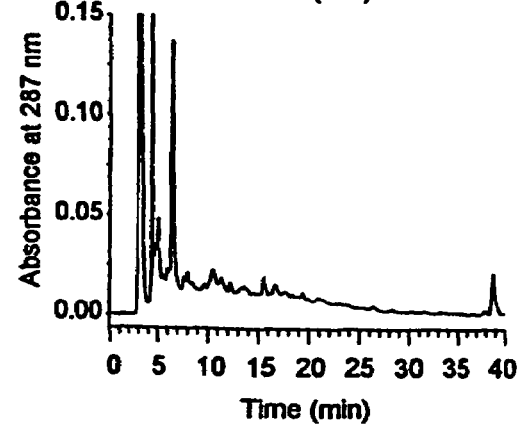
Figure 5E:
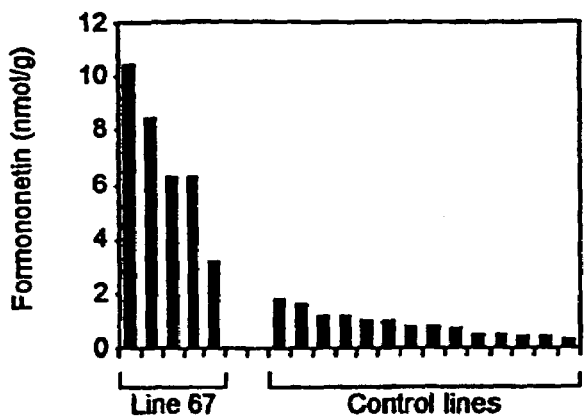
Figure 5F:
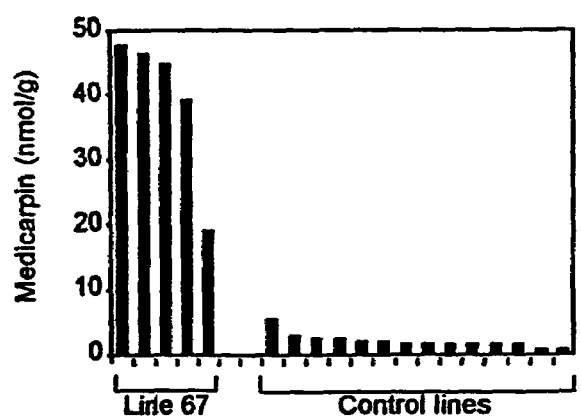
Figure 5G:
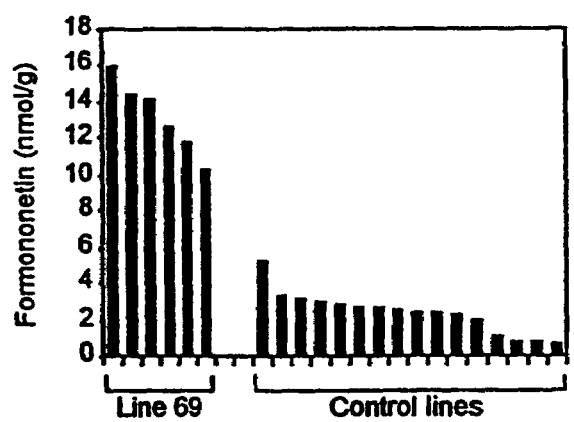
Figure 5H:
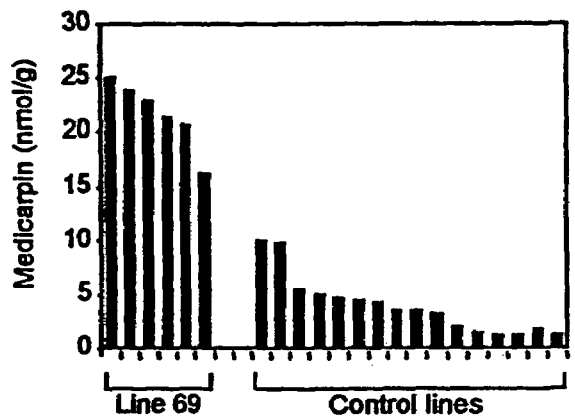

Cuttings were taken from sense lines #67 and #69, and from a range of untransformed and empty vector control lines, and propagated in the growth chamber. To induce the enzymes of the isoflavonoid pathway, trifoliate leaves were elicited by exposure to 3 mM $CuCl_2$ taken up through the cut petioles for 8 hours at room temperature. This is a reliable method for induction of isoflavonoid accumulation in alfalfa (Dewick, P. M. and Martin, M. 1979. "Biosynthesis of pterocarpan and isoflavan phytoalexins in *Medicago sativa* the biochemical interconversion of pterocarpans and 2'-hydroxy-isoflavans," *Phytochemistry* 18: 591-596). Trifoliate leaves were placed on 2 layers of moist filter paper in a petri dish and incubated for a further 24 hours. Levels of induced isoflavonoids were then determined by HPLC as described above. Leaves that had not been exposed to copper contained no detectable formononetin or medicarpin, as depicted in FIGS. 5C and 5D. Copper treatment led to a modest induction, of formononetin and medicarpin in the various control lines, but to much stronger induction in the IOMT over-expressing lines (FIGS. 5A and 5B). Analysis of replicate cuttings from each of the lines clearly indicated that over-expression of IOMT in elicited alfalfa leaves leads to a significant increase in the levels of formononetin and medicarpin if the isoflavonoid pathway is first induced by elicitation (FIGS. 5C and 5H). Importantly, when the IOMT activity was measured in extracts from control or $CuCl_2$-elicited leaves of the various lines, the product was always isoformononetin, indicating that $CuCl_2$ itself does not affect the regiospecificity of the enzyme. No isoformononetin was observed in any of the elicited leaf samples.

Figure 6A:
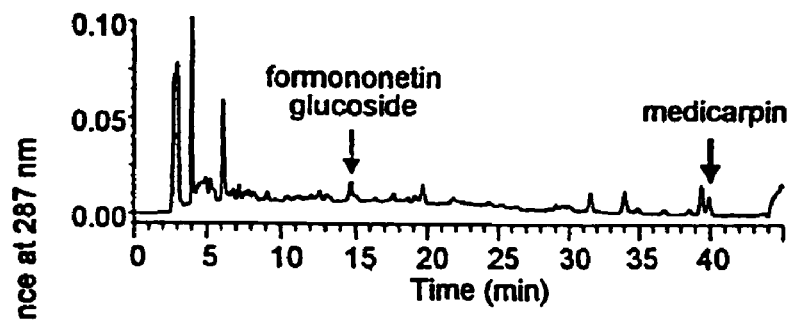
FIG. 6A-6F depict accumulation of isoflavonoid compounds in response to fun gal infection in control and IOMT over-expressing transgenic alfalfa.
Figure 6B:
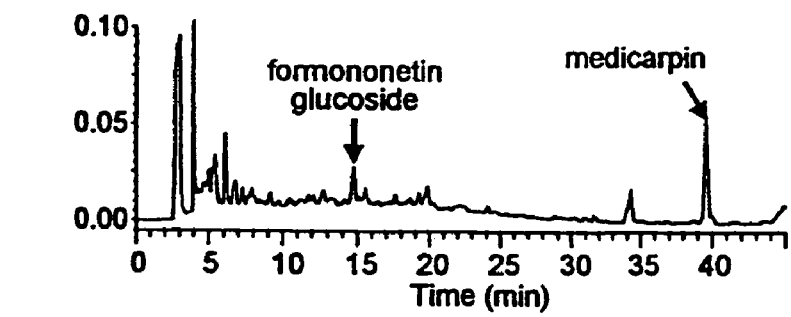
Figure 6C:
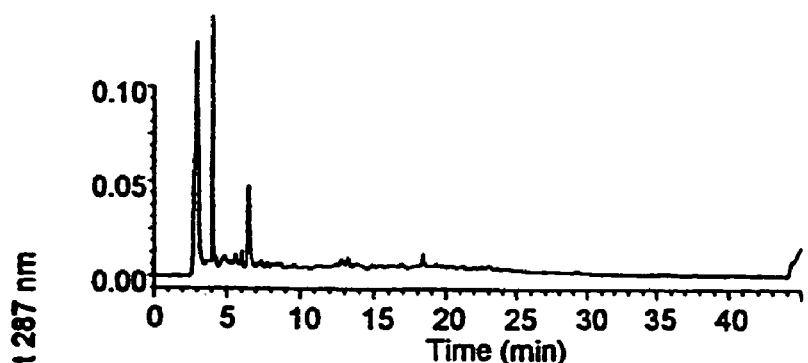
Figure 6D:
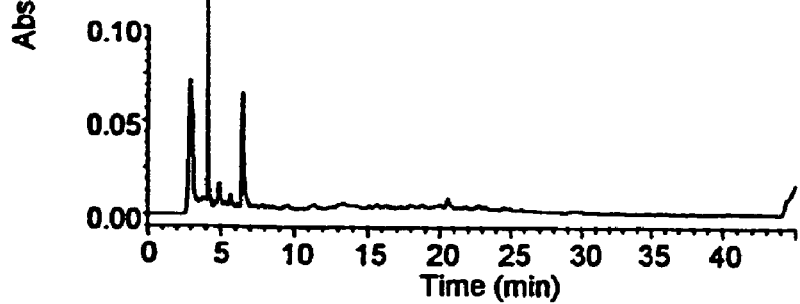
Figure 6E:
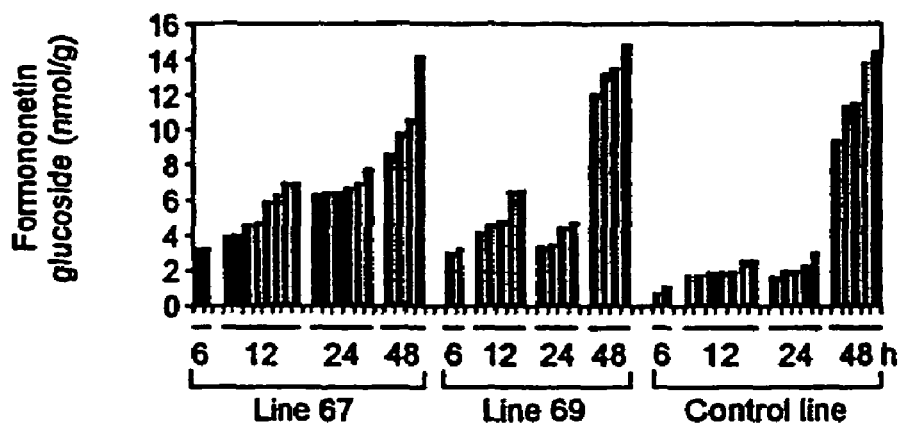
Figure 6F:
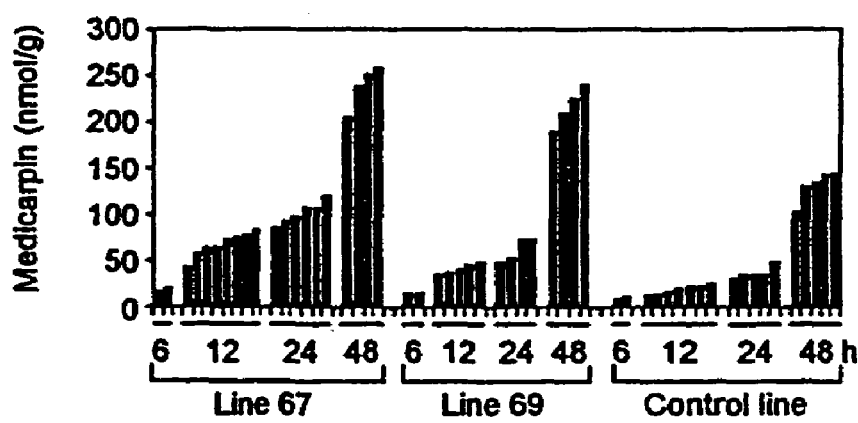

The above experiments were repeated using infection by spores of *Phoma medicaginis*, a treatment that induces the enzymes of the isoflavonoid pathway and consequent medicarpin accumulation in alfalfa leaves (Paiva, et al. 1994. *Plant Cell, Tissue and Organ Cult* 38: 213-220). Metabolite profiles for leaves from control empty vector and IOMT over-expressing (line #67) plants after exposure to *P. medicaginis* are shown in FIGS. 6A and 6B, respectively. Fungal infection led to appearance of formononetin glucoside and medicarpin in the control lines (FIG. 6A), but much stronger induction in the IOMT over-expressing lines (FIG. 6B), and no isoformononetin was observed in any of the infected leaf samples (FIG. 6B). No formononetin glucoside or medicarpin were observed in uninfected control plants (FIGS. 6C and 6D). Analysis of replicate cuttings from each of the lines, harvested at various time after fungal infection, clearly indicated that over-expression of IOMT in infected alfalfa leaves leads to earlier induction and increased levels of formononetin glucoside and medicarpin compared to control lines (FIGS. 6E and 6F).

Figure 7A:
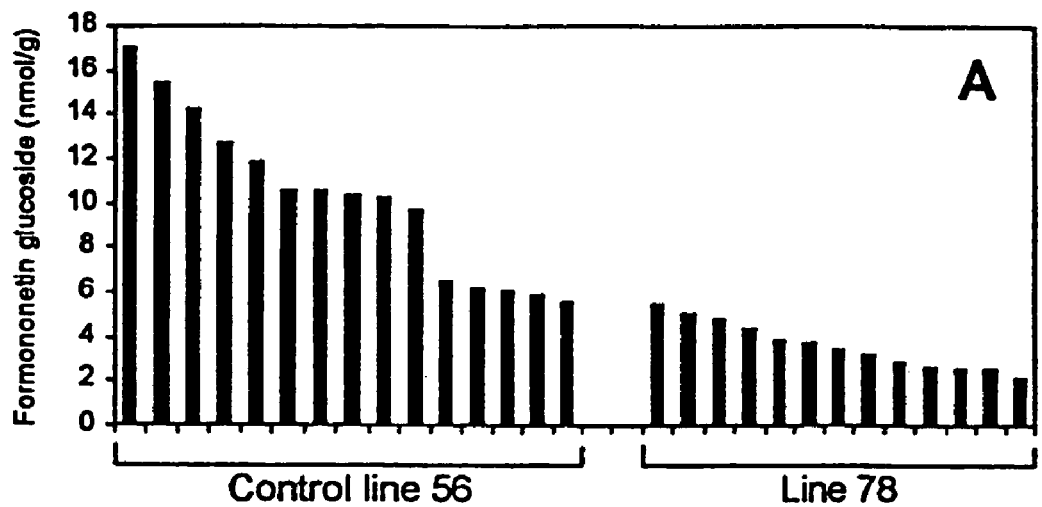
FIG. 7A-7B depict accumulation of isoflavonoid compounds in control and putatively IOMT gene-silenced transgenic alfalfa Levels of formononetin glucoside (FIG. 7A) and medicarpin (FIG. 7B) were measured in leaves from replicate cuttings of vector control line #56C and IOMT sense transformant #78 20 hr after inoculation with spores of *Phoma medicaginis*.
Figure 7B:
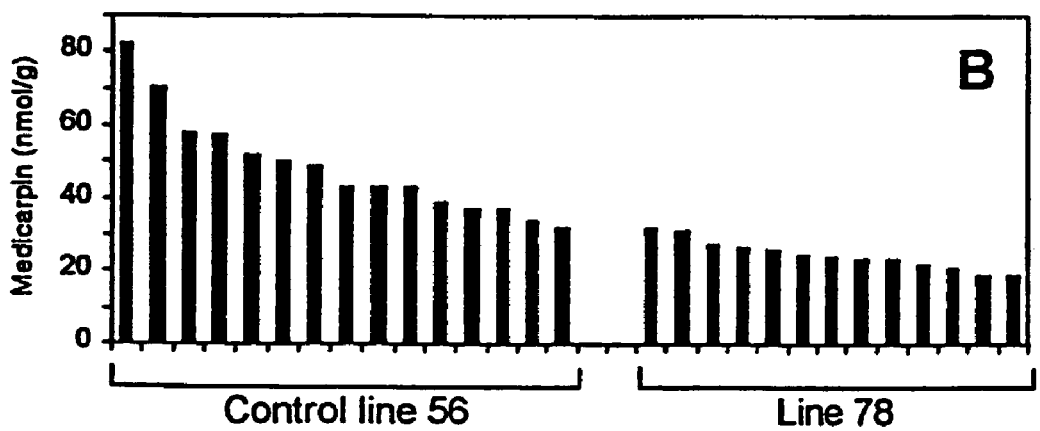

Sense transformant #78 had a high transgene copy number but did not express IOMT protein in the leaves (FIG. 3B). It appeared to exhibit epigenetic gene silencing (Matzke, M. A. and A. J. M. Matzke. 1995. "How and why do plants inactivate homologous (trans)genes?" *Plant Physiol* 107: 679-685). Analysis of replicate cuttings of line #78 and empty vector control line #56C indicated that, following infection with *P. medicaginis*, induction of formononetin glucoside and medicarpin in line #78 was significantly less than in the control plants (FIGS. 7A and 7B). Overall, the reductions were by 65% for formononetin conjugate and 58% for medicarpin, and this reflected the relative IOMT activities in plants of the two lines. Thus, the data on the up- and down-regulation of IOMT in elicited or infected alfalfa leaves indicate that, if the remainder of the isoflavonoid pathway is induced, IOMT functions operationally in the formation of 4'-O-methylated isoflavonoids (formononetin and medicarpin in alfalfa) rather than as a 7-O-methyltransferase producing isoformononetin.

Figure 8A:
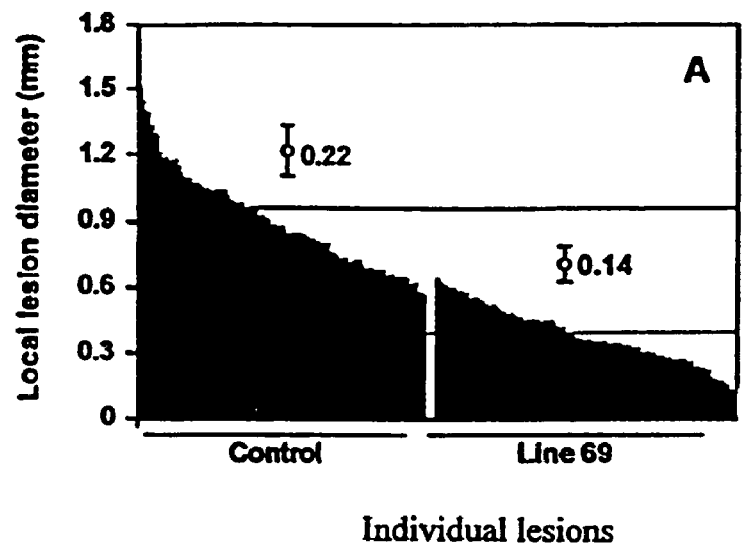
FIG. 8A-8B depict disease resistance of transgenic alfalfa modified in expression of isoflavone O-methyltransferase.
Figure 8B:
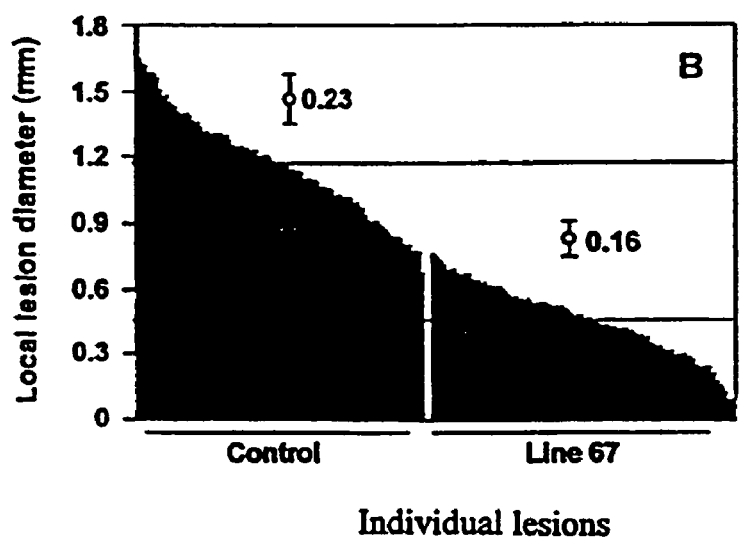

*Phoma medicaginis* is a successful pathogen of alfalfa, leading to disease symptoms on the cultivar (Regen SY) used for the genetic transformation. To determine whether the more rapid accumulation of the phytoalexin medicarpin leads to resistance to *Phoma* in plants over-expressing IOMT, IOMT over-expressing and control plants were inoculated on the leaves using a pin wheel to produce a line of small wounds, into which fungal spores would enter to initiate infection on the susceptible alfalfa cultivar. The sizes of the brown *Phoma* lesions were then measured at 5 days post-infection. The results showed that the lesion size was much reduced in the IOMT over-expressing lines #67 and #69 compared to the controls. Measurement of multiple lesions five days after infection gave an average lesion size of 0.96 mm (n=100) for control plants and 0.41 mm (n=100) for line #69, and 0.46 mm (n=100) for IOMT over-expressing line #67 compared to 1.17 mm (n=100) for the corresponding control line grown and infected in parallel, as shown in FIGS. 8A and 8B. Thus, transgenic over-expression of IOMT is a viable strategy for engineering disease resistance in alfalfa, and, by analogy, in other plants in which 4'-O-methylated isoflavonoids serve as phytoalexins.

Taken together, the results of the enzyme assays, feeding, elicitation and infection studies with transgenic alfalfa indicate that IOMT methylates the 7-position of daidzein to produce isoformononetin from exogenously supplied daidzein both in vitro and in planta, but is involved in 4'-position specific methylation to produce formononetin when the daidzein is supplied through the endogenous isoflavonoid pathway in planta. By performing reverse genetic experiments to modify expression of the enzyme in transgenic plants that naturally contain this enzyme, this unusual differential regiospecificity of IOMT in vivo compared to in vitro has now been found.

Up- and down-regulation of IOMT expression in transgenic alfalfa has quantitatively corresponding effects on the levels of 4'-O-methylated isoflavonoids, indicating that IOMT operates functionally as a rate limiting enzyme for the synthesis of these compounds in alfalfa. In contrast, it has been previously reported that the major rate-limiting step in isoflavonoid biosynthesis is at the entry point into the isoflavonoid branch pathway catalyzed by the isoflavone synthase cytochrome P450 (Steele et al. 1999. "Molecular characterization of the enzyme catalyzing the aryl migration reaction of isoflavonoid biosynthesis in soybean," *Arch Biochem Biophys* 367: 146-150; and Jung, et al. 2000. "Identification and expression of isoflavone synthase, the key enzyme for biosynthesis of isoflavones in legumes," *Nature Biotechnology* 18: 208-212).

The above data suggest that increased production of 4'-O-methylated isoflavonoids and resultant disease resistance in IOMT over-expressing plants might be the direct result of elevated IOMT levels, and, therefore, point to a direct involvement of IOMT in the synthesis of these compounds as a rate limiting step. However, because the 4'-O-methylated compounds are stress-induced phytoalexins in alfalfa, it is possible that lines with elevated IOMT activity have some kind of metabolic stress that leads to increased phytoalexin production, independent of flux through IOMT. This is unlikely in view of the lack of detectable phytoalexins in unelicited or uninfected IOMT over expressing plants (FIGS. 5C and 5D, and FIGS. 6C and 6D). To further rule out this possibility, and to determine whether other enzymes of the isoflavonoid pathway might be modulated following expression of IOMT, we examined the levels of transcripts encoding eight of the enzymes involved in the conversion of phenylalanine to medicarpin in a control and an IOMT over-expressing line as a function of time following infection with *P. medicaginis*. The results in Table I confirm, firstly, that IOMT transcripts were constitutively high in line #69 in the absence of *Phoma* infection, consistent with the transgene being under control of the 35S promoter. In uninfected leaves ectopically expressing IOMT, the levels of transcripts of the other enzymes of the phenylpropanoid/isoflavonoid pathway were not significantly elevated above control levels. Thus, overexpression of IOMT does not, of itself, induce the isoflavonoid pathway as a stress response, consistent with the metabolic profile data of FIGS. 5 and 6.

RNA gel blot analysis of isoflavonoid pathway transcripts in *Phoma* infected leaves of empty vector control (line #64C) and IOMT over-expressing (line #69) alfalfa using labeled cDNA for various enzymes in the isoflavonoid pathway is given in Table I. Total RNA was isolated from leaves at 6,24 and 48 hours after infection with *P. medicaginis* (Lane P) or treatment with water (Lane W), and probed with labeled cDNA probes for alfalfa PAL, alfalfa C4H, alfalfa acetyl CoA carboxylase, alfalfa CHI, *Medicago truncatula* IFS, alfalfa IOMT, *Medicago truncatula* I2'OH and alfalfa IFR. Blots were stripped and re-probed with a ribosomal RNA probe to check loading and transfer efficiency. Following infection with *Phoma*, there was a weak, relatively slow induction of phytoalexin pathway enzyme transcripts in empty vector control alfalfa leaves. This response is typical of that found in compatible interactions (Lamb, et al. 1992. "Emerging strategies for enhancing crop resistance to microbial pathogens," *Bio/technology* 10: 1436-1445). However, the levels of transcripts encoding phenylalanine ammonia-lyase (PAL), cinnamate 4-hydroxylase (C4H), and isoflavone reductase (IFR) were much greater in IOMT over-expressing Line #69 than in the control line by 12 hours post-infection. These transcripts were also significantly induced in Line #69 by 6 hours post-infection, whereas IFS and IFR transcripts remained uninduced by 6 hours post-treatment in the control. Levels of chalcone isomerase (CHI) and isoflavone 2'-hydroxylase (I2'OH) transcripts were slightly elevated in Line #69 compared to the control following infection. In contrast, transcripts encoding cytosolic acetyl CoA carboxylase, the enzyme that provides malonyl CoA for the chalcone synthase reaction and that is co-induced as part of the phytoalexin response in elicited alfalfa cells (Shorrosh, et al. 1994. "Molecular cloning, characterization and elicitation of acetyl-CoA carboxylase in alfalfa," *Proc Natl Acad Sci USA* 91: 4323-4327), were not significantly higher in Line #69 than in the empty vector control line under any of the treatments.

TABLE I

RNA Gel Blot Analysis of Isoflavonoid Pathway Transcripts in Phoma Infected Leaves of Empty Vector Control (Control)[a] and IOMT Over-expressing (Line #69) Alfalfa Over Time[b]

| | | Time post-treatment | | | | | |
|---|---|---|---|---|---|---|---|
| | | 6 hours | | 12 hours | | 24 hours | |
| Enzyme[c] | Line | Phoma infection | Water treatment | Phoma infection | Water treatment | Phoma infection | Water treatment |
| PAL | #69 | 7 | 1 | 9 | 1 | 4 | 4 |
| | Control | 4 | 1 | 6 | 1 | 4 | 1 |
| C4H | #69 | 7 | 4 | 9 | 3 | 5 | 5 |
| | Control | 2 | 1 | 7 | 1 | 2 | 1 |
| ACC | #69 | 4 | 2 | 7 | 5 | 4 | 4 |
| | Control | 4 | 4 | 7 | 2 | 4 | 2 |
| CHI | #69 | 7 | 7 | 9 | 6 | 6 | 0 |
| | Control | 6 | 6 | 8 | 5 | 6 | 1 |
| IFS | #69 | 2 | 0 | 7 | 2 | 6 | 2 |
| | Control | 0 | 0 | 6 | 0 | 3 | 1 |
| IOMT | #69 | 3 | 3 | 3 | 3 | 3 | 3 |
| | Control | 0 | 0 | 3 | 0 | 1 | 0 |
| I2'OH | #69 | 6 | 4 | 9 | 4 | 5 | 4 |
| | Control | 4 | 4 | 9 | 1 | 4 | 1 |

TABLE I-continued

RNA Gel Blot Analysis of Isoflavonoid Pathway
Transcripts in Phoma Infected Leaves of Empty
Vector Control (Control)[a] and IOMT Over-expressing (Line #69) Alfalfa Over Time[b]

| | | Time post-treatment | | | | | |
|---|---|---|---|---|---|---|---|
| | | 6 hours | | 12 hours | | 24 hours | |
| Enzyme[c] | Line | Phoma infection | Water treatment | Phoma infection | Water treatment | Phoma infection | Water treatment |
| IFR | #69 | 6 | 0 | 9 | 0 | 7 | 1 |
| | Control | 0 | 0 | 7 | 0 | 1 | 0 |

[a]Control = Line #64C.
[b]Results of RNA gel blots are reported in terms of relative intensity of bands.
[c]Enzymes: alfalfa PAL (L-phenylalanine ammonia-lyase); alfalfa C4H (cinnamate 4-hydroxylase); alfalfa ACC (cytosolic acetyl CoA carboxylase); alfalfa CHI (chalcone isomerase); *Medicago truncatula* IFS (isoflavone synthase); alfalfa IOMT (isoflavone-O-methyltransferase); *Medicago truncatula* I2'OH (isoflavone 2'-hydroxylase); and alfalfa IFR (isoflavone reductase).

In various embodiments, IOMT genes can be introduced into plants by standard plant transformation strategies including, but not limited to, *Agrobacterium*-mediated transformation (Horsch, B. et al. 1985. "A simple and general method for transferring genes into plants," *Science* 227: 1229-1231) or particle bombardment (Klein, et al. 1988. "Stable genetic transformation of intact *Nicotiana* cells by the particle bombardment process," *Proc Natl Acad Sci USA* 85: 8502-8505).

In the present invention, any polynucleotide encoding IOMT having the property to induce the production of 4-O-methylated phytoalexins, nutraceuticals, their conjugates or mixtures thereof can be utilized. A polynucleotide encoding IOMT useful in the present invention includes the sequence in SEQ ID NO:1 and FIG. 2, polynucleotides encoding dominant negative forms of IOMT, and nucleic acid sequences complementary to the sequence in SEQ ID NO:1 and FIG. 2. A complementary sequence may include an antisense nucleotide. When the sequence is RNA, the deoxynucleotides A, G, C, and T of the sequence in SEQ ID NO:1 and FIG. 2 are replaced by ribonucleotides A, G, C, and U, respectively. Also included in the invention are fragments of the above-described nucleic acid sequences which are of sufficient nucleotide length to permit the fragment to selectively hybridize to DNA that encodes the protein of the sequence in SEQ ID NO:1 and FIG. 2 under physiological conditions or a close family member of IOMT. Degenerate variants of the sequence in SEQ ID NO:1 and FIG. 2, the sequence in SEQ ID NO:1 and FIG. 2 where T can also be a U, and fragments of these sequences that will hybridize to DNA or RNA which encodes IOMT are also included. The term "selectively hybridize" refers to hybridization under moderately or highly stringent conditions which excludes non-related nucleotide sequences.

Rate control by IOMT allows for manipulation of IOMT expression to drive increased accumulation of antimicrobial phytoalexins as a mechanism for improved plant disease resistance, or to increase or decrease the levels and/or methylation status of isoflavones. Isoflavones are valuable as nutraceuticals (Adlercreutz, H. and W. Mazur. 1997. "Phyto-estrogens and western diseases," *Ann Med* 29: 95-120), and are naturally limited to the *leguminosae*, where they occur with the 4'-hydroxyl group methylated (formononetin and biochanin A) or free (daidzein and genistein). Modification of IOMT expression in vivo can be used to alter the 4'-O-methylation of a plant's isoflavones. As used herein, 4'-O-isoflavonoid phytoalexins include but are not limited to medicarpin, maackiain, pisatin, their respective conjugates, or mixtures thereof; and 4'-O-methylated isoflavonoid nutraceuticals include but are not limited to formononetin, biochanin A, texasin, afromosin, pseudobaptigenin, their respective conjugates, or mixtures thereof. Increases in levels of 4'-O-isoflavonoid phytoalexins and 4'-O-methylated isoflavonoid nutraceuticals can be made by over-expression of the IOMT gene in transgenic plants which naturally make these compounds and by expression of the IOMT gene in transgenic plants which naturally do not make these compounds. Furthermore, 4'-O-methylated isoflavonoid nutraceuticals can be produced in non-plant systems (including but not limited to transfected bacterial, yeast or insect cells which have been genetically transformed to contain all the other necessary enzymes of isoflavonoid biosynthesis) by expression of the IOMT gene under the control of a suitable constitutive or inducible promoter using methods known in the art (Frick, S., Kutchan, T. M. 1999. "Molecular cloning and functional expression of O-methyltransferases common to isoquinoline alkaloid and phenylpropanoid biosynthesis," *Plant J* 17: 329-339; Batard, et al. 1998. "Molecular cloning and functional expression in yeast of CYP76B1, a xenobiotic-inducible 7-ethoxycoumarin O-de-ethylase from *Helianthus tuberosus*," *Plant J* 14: 111-120).

The present invention also includes a composition comprising at least one 4'-O-methylated isoflavonoid suitable for administration as a food stuff, a nutritional supplement, an animal feed supplement, a nutraceutical, or a pharmaceutical, wherein the source of the 4'-O-methylated isoflavonoid is a transgenic plant expressing an isoflavone O-methyltransferase gene of the present invention. A portion of the transgenic plant comprising the 4'-O-methylated isoflavonoid or 4'-O-methylated isoflavonoid extracted from the transgenic plant can be utilized.

For down-regulation of IOMT in plants that naturally make 4'-O-isoflavonoid phytoalexins and 4'-O-methylated isoflavonoid nutraceuticals, IOMT gene sequences can be transformed in the antisense orientation (Bourque, J. E. 1995. "Antisense strategies for genetic manipulations in plants," *Plant Sci* 105: 125-149) or expressed from vectors designed to activate gene silencing (Angell, S. M. and D. C. Baulcombe. 1997. "Consistent gene silencing in transgenic plants expressing a replicating potato virus X RNA," *EMBO J* 16: 3675-3684). IOMT sequences used can be the alfalfa IOMT8 designated in SEQ ID NO:1 and FIG. 2, or any other IOMT gene with in vivo 4'-O-methylation specificity that could be isolated by hybridization techniques using IOMT8 as a probe.

Isoflavonoid compounds methylated at the 7-position (e.g., isoformononetin and prunetin) may also have nutraceutical activity, and the alfalfa IOMT can be used for making these compounds by feeding non-methylated isoflavone precursors to intact plants, plant cell suspension cultures, or non-plant systems (including but not limited to transfected bacterial, yeast or insect cells which have been genetically transformed to contain all the other necessary enzymes of isoflavonoid biosynthesis) which have been transformed with an IOMT gene under the control of a suitable constitutive or inducible promoter. Alternatively, the 7-O-methylated isoflavonoid compounds can be produced using in vitro processes by contacting non-methylated isoflavone precursors with isolated soluble or immobilized isoflavone-O-transferase enzyme which has been produced and isolated from transgenic plants, plant cell suspension cultures or a non-plant system (including but not limited to transfected bacterial, yeast or insect cells which have been genetically transformed to contain all the other necessary enzymes of isoflavonoid biosynthesis). As used herein, 7-O-methylated isoflavonoid compounds include but are not limited to isoformononetin, prunetin, their respective conjugates, or mixtures thereof.

We claim:

1. A method for the production of a 7-O-methylated isoflavonoid compound comprising contacting intact plants or cell suspension cultures with a non-methylated isoflavone precursor of said 7-O-methylated isoflavonoid compound, wherein the precursor is a substrate for an enzyme comprising the polypeptide sequence encoded by SEQ ID NO:1, said intact plants or cell suspension cultures transformed with a DNA fragment comprising an isoflavone O-methytransferase gene under the control of a suitable constitutive or inducible promoter, wherein said DNA fragment is selected from the group consisting of: a DNA fragment comprising SEQ ID NO:1; a DNA fragment that encodes the polypeptide encoded by SEQ ID NO:1; and a DNA fragment comprising a sequence that hybridizes with SEQ ID NO:1 under wash conditions of 0.2×SSC, 0.1% SDS at 65° C.

2. A method for the production of a 7-O-methylated isoflavonoid compounds comprising contacting a soluble or immobilized isoflavone O-methytransferase enzyme with a non-methylated isoflavone precursor to said 7-O-methylated isoflavonoid compound, wherein the precursor is a substrate for an enzyme comprising the polypeptide sequence encoded by SEQ ID NO:1, wherein said enzyme is produced by the expression of a DNA fragment encoding the isoflavone O-methyltransfer gene in transgenic plants, transfected yeast, or transfected insect cells, wherein said DNA fragment is selected from the group consisting of: a DNA fragment comprising SEQ ID NO:1; a DNA fragment that encodes the polypeptide encoded by SEQ ID NO:1; and a DNA fragment comprising a sequence that hybridizes with SEQ ID NO:1 under wash conditions of 0.2×SSC, 0.1% SDS at 65° C.

3. The method of claim 1, wherein the intact plants or cell suspension cultures are from a legume plant.

4. The method of claim 3, wherein the legume is alfalfa.

5. The method of claim 1, wherein the DNA fragment encodes the polypeptide encoded by SEQ ID NO:1.

6. The method of claim 1, wherein the DNA fragment hybridizes with SEQ ID NO:1 under wash conditions of 0.2×SSC, 0.1% SDS at 65° C.

7. The method of claim 2, wherein the enzyme comprises the polypeptide sequence encoded by SEQ ID NO:1.

8. The method of claim 2, wherein the DNA fragment hybridizes with SEQ ID NO:1 under wash conditions of 0.2×SSC, 0.1% SDS at 65° C.

9. The method of claim 1, wherein the DNA fragment comprises SEQ ID NO:1.

10. The method of claim 2, wherein the DNA fragment comprises SEQ ID NO:1.

\* \* \* \* \*

UNITED STATES PATENT AND TRADEMARK OFFICE
CERTIFICATE OF CORRECTION

PATENT NO. : 7,432,425 B2
APPLICATION NO. : 11/071964
DATED : October 7, 2008
INVENTOR(S) : Dixon et al.

It is certified that error appears in the above-identified patent and that said Letters Patent is hereby corrected as shown below:

On the Title Page, Item (57) in the Abstract, line 1, delete "biology" and insert --biologically--.

In Claim 2, column 21, line 53, delete "compounds" and insert --compound--.

In Claim 2, column 21, line 60, delete "O-methyltransfer" and insert --O-methyltransferase--.

Signed and Sealed this

Twenty-seventh Day of January, 2009

JOHN DOLL
*Acting Director of the United States Patent and Trademark Office*